US008201941B2

(12) United States Patent
Choo et al.

(10) Patent No.: US 8,201,941 B2
(45) Date of Patent: Jun. 19, 2012

(54) CORNEAL AND EPITHELIAL REMODELLING

(75) Inventors: Jennifer Denise Choo, Randwick (AU); Arthur Ho, Coogee (AU); William E. Meyers, Scottsdale, AZ (US); Fabian Conrad, Maroubra (AU); Brien Anthony Holden, Kensington (AU)

(73) Assignee: The Institute For Eye Research

( * ) Notice: Subject to any disclaimer, the term of this patent is extended or adjusted under 35 U.S.C. 154(b) by 250 days.

(21) Appl. No.: 12/309,841

(22) PCT Filed: Jul. 31, 2007

(86) PCT No.: PCT/AU2007/001063
§ 371 (c)(1), (2), (4) Date: Aug. 4, 2009

(87) PCT Pub. No.: WO2008/014544
PCT Pub. Date: Feb. 7, 2008

(65) Prior Publication Data
US 2009/0303442 A1    Dec. 10, 2009

(30) Foreign Application Priority Data
Jul. 31, 2006   (AU) ................................ 2006904125

(51) Int. Cl.
*G02C 7/04* (2006.01)

(52) U.S. Cl. .................................... 351/160 R; 351/177
(58) Field of Classification Search .............. 351/160 R, 351/160 H, 161, 162, 177
See application file for complete search history.

(56) References Cited

U.S. PATENT DOCUMENTS 5,963,297 A * 10/1999 Reim ...................... 351/160 R
6,582,077 B1    6/2003 Tabb et al.
(Continued)

FOREIGN PATENT DOCUMENTS
WO    WO 97/34185    9/1997
(Continued)

OTHER PUBLICATIONS

Carkeet NL; *Predicting success with orthokeratology lens wear; a retrospective analysis of ocular characteristics*, Optometry and Vision Science, vol. 72, No. 12, 892,898, Dec. 1995.

(Continued)

*Primary Examiner* — Scott J Sugarman
(74) *Attorney, Agent, or Firm* — Morgan, Lewis & Bockius LLP

(57) ABSTRACT

This invention relates to methods of shaping the anterior surface of the eye for controlling the progression of refractive error of the eye, in particular, myopia. The method employs the fitting of orthokeratology lenses having a precisely shaped posterior surface adapted to accurately shape the peripheral region of the eye. The method includes the steps of assessing central and peripheral refractive error parameters for the eye, determining the optimal anterior surface profile for the eye, including at both the optical centre of the cornea and at a selected optical periphery of the cornea, which would result in a desired refractive correction to achieve good vision for the eye and the desired peripheral refraction (curvature of field) for the eye for controlling progression of myopia. Accurate measurement of the shape of the pre-treated eye is important, thereby enabling a corresponding lens profile to be designed or selected so that the treatment process achieves a post-treatment peripheral profile which optimally focuses peripheral rays anteriorly of the retina, thereby controlling the progression of myopia. The invention extends to a lens manufactured so as to optimally treat the peripheral region of the eye.

14 Claims, 23 Drawing Sheets

Composite BC design including edge segments

U.S. PATENT DOCUMENTS

| | | | |
|---|---|---|---|
| 7,025,460 B2 | 4/2006 | Smitth et al. | |
| 2003/0095232 A1 | 5/2003 | Mitsui | |
| 2007/0115431 A1* | 5/2007 | Smith et al. | 351/221 |

FOREIGN PATENT DOCUMENTS

| | | |
|---|---|---|
| WO | WO 2002/041070 A1 | 5/2002 |
| WO | WO 2005/022242 A1 | 3/2005 |
| WO | WO 2005/055891 A1 | 6/2005 |

OTHER PUBLICATIONS

Swarbrick, Helen A; *Orthokeratology review and update*; Clinical & Experimental Optometry, vol. 89, No. 3, pp. 124-143; May 2006.

International Search Report and Written Opinion issued in PCT/AU2007/001063 on Sep. 18, 2007.

The Institute for Eye Research, Supplemental European Search Report, EP 07784708.5, Sep. 12, 2011, 4 pgs.

* cited by examiner

CORNEAL AND EPITHELIAL REMODELLING

CROSS REFERENCE TO RELATED APPLICATIONS

This Application is a United States National Stage Application filed under 35 U.S.C. §371 of PCT Patent Application Serial No. PCT/AU2007/001063 filed on Jul. 31, 2007, which claims the benefit of and priority to Australian (AU) Patent Application Serial No. 2006904125 filed on Jul. 31, 2006, the disclosures of both of which are hereby incorporated by reference in their entirety.

FIELD OF THE INVENTION

This invention relates to methods of shaping the anterior surface of the eye for controlling the progression of refractive error of the eye. The method may employ the use of orthokeratology lenses, although other shaping techniques are also envisaged.

BACKGROUND OF THE INVENTION

In the treatment of visual acuity deficiencies, correction by means of eyeglasses or contact lenses is used by a large percentage of the population. Such deficiencies include patients having hyperopia or being far-sighted, myopia or near-sighted patients as well as astigmatisms caused by asymmetry of the patient's eye. More recently, to alleviate the burden of wearing eyeglasses and/or contact lenses, surgical techniques have been developed for altering the shape of the patient's cornea in an attempt to correct refractive errors of the eye. Such surgical techniques include photo-refractive keratectomy (PRK), LASIK (laser in-situ keratomileusis), as well as procedures such as automated lamellar keratectomy (ALK) or others. These procedures are intended to surgically modify the curvature of the cornea to reduce or eliminate visual defects. The popularity of such techniques has increased greatly, but still carries the risk in both the procedure itself as well as post-surgical complications.

An alternative to permanent surgical procedures to alter the shape of the cornea include orthokeratology, where a contact lens is applied to the eye to temporarily alter the shape or curvature of the cornea by mechanical reshaping of the corneal surface imparted by the lens. The reshaping of the cornea in orthokeratology has been practised for many years, but typically has required an extensive period of time to reshape the cornea.

Whilst orthokeratology lenses (orthokeratology lenses) have been used for many years, the manner in which such lenses operate, and in particular the physiology of the process of corneal reshaping, is still not fully understood. There is no consensus on the optimal shape for such lenses, and because no two eye shapes or refractive error parameters are the same, selecting an optimal lens shape for a particular patient is, at least to some extent, an intuitive rather than a prescriptive process.

Other corneal shaping techniques, such as those discussed above, also require a precise understanding of the optimal shape of the eye. It will be appreciated that, because differences of a few microns in thickness at different positions in the eye can make a significant difference to the efficacy of any treatment, an improved understanding of the optimal shape for any particular eye is considered to be important.

Typically, the treating of eyes to achieve improved vision using the techniques discussed above have concentrated on focusing light entering the eye along its axis, that is, from the point in space that the eye is 'looking at'. However, it has recently been suggested that to control the progression of the refractive error it is not only important to optimally focus this central or axial light, but also to control the focus of light entering the eye at an angle, that is, coming from points in the visual space away from the direction the eye is 'looking'—sometimes called peripheral vision. In optical engineering parlance, light rays travelling from points away from the direction of view of the eye are called off-axis rays, and the points in space representing peripheral vision is also called the mid-peripheral and peripheral field, and the 'surface' described by the collection of peripheral foci at the different peripheral field angles is called the curvature of field. The patent application, US 2005/0105047 (Smitth) discusses the importance of positioning peripheral, off-axis focal points, relative to the central, on-axis focal point for retarding or abating the progression of myopia or hypermetropia.

Thus, it will be apparent that a fairly wide region of the eye influences the long-term refractive state of the eye. Any process which reshapes the eye to correct only central field to achieve acute vision and yet ignores the effect that off-axis peripheral field light entering the eye may have, could potentially be damaging to its long-term refractive state. Thus, a treatment regime or process which produces an optimal shape over the whole optical surface of the eye is considered important.

Recent clinical studies have suggested a link between myopia control and the use of orthokeratology lenses in children. The inventors are aware of only three publications (as summarised below) that have addressed this issue.

1) Cho et al. (2005)
   a. 2 year prospective pilot study with a historical control group
   b. 7 to 12 year olds
   c. 43 enrolled, 35 completed study
   d. Difference in axial length and vitreous chamber depth between OK and control groups
      i. About 52% treatment effect in OK treated eyes
   e. Conclusions: OK can have both corrective and control effect in childhood myopia but there are substantial variations in changes in eye length among children and there is no way to predict the effect for individual subjects
   f. Limitations: not randomized, no masking, no standard lens fitting protocol
2) Cheung et al (2004)
   a. Case report: 13 year old Asian male examined over 2 years
   b. Monocular OK treatment
   c. Conclusions: eye with OK grew less than eye without treatment
   d. Limitations: patient had uneven refractive errors to begin with and the eye without treatment may have been trying to "catch up" to the myopic eye
   e. No control, case report
3) Reim (2003)
   a. Retrospective case series
   b. Only looked at change in refraction at 1 or 3 years after 3 months of stable OK wear
   c. 253 subjects at 1 year, 164 subjects at 3 years
   d. Conclusions: rate of myopia progression similar to GPs in Stone/Grosvenor/Koo study
   e. Limitations: no controls, no axial growth measurements The only controlled study was the pilot conducted by Cho et al which still requires confirmation through a larger study. However, their findings suggest that orthokeratology may slow the growth of the eye but it does not work for all children. No one fully understands why orthokeratology gave a myopia control effect in only some of the children in that study.

To date, the inventors are not aware of any studies directed to the specific optics related to orthokeratology. Many have attempted to analyse the shape of the cornea via topographical analyses, but few have attempted to quantify and describe the exact corneal shape or profile for good vision (e.g. 6/6 vision), let alone myopia control.

US Patent Application 2005/0105047 (Smitth) describes optical intervention to control myopia progression. The publication discloses the optical 'profile' required to cease myopia growth and identified some techniques and devices which could be used. However, it has been determined that not all patients respond in the same way to treatment, and whilst some patients, for example, who undergo an orthokeratology treatment will show a slowing down or halting of myopia progression whilst they are receiving orthokeratology treatment, others will show that orthokeratology treatment has almost no effect on myopia progression.

SUMMARY OF THE INVENTION

In broad terms the invention provides a method of changing the focus of incoming peripheral light rays into an eye in a controlled and predictable manner to slow, halt or reverse the progression of myopia in a myopic patient using an orthokeratology lens. Specifically the specification teaches methodologies and design parameters to facilitate and enable the design and production of orthokeratology lenses which will enable the method to be effectively carried out.

According to a preferred aspect of the invention there is provided a method of altering the profile of the anterior surface region of an eye of a patient to achieve improved vision for the patient, including the steps of:
assessing central and peripheral refractive error parameters for the eye;
determining the optimal anterior surface profile for the eye, including at both the optical centre of the cornea and at the effective optical periphery of the cornea, which would result in a desired refractive correction to achieve good vision for the eye and the desired peripheral refraction (curvature of field) for the eye for controlling progression of refractive error; and
treating the eye of the patient with an orthokeratology lens to achieve said optimal anterior surface profile.

Preferably the step of treating the eye of the patient involves applying an orthokeratology lens to the eye, the method including selecting a lens which has characteristics which will shape the anterior surface of the eye to achieve said optimal anterior surface profile. The lens preferably has characteristics which will result in the epithelial volume of the eye being preserved.

The desired peripheral refraction (curvature of field) optionally places the peripheral retinal image more anteriorly than the retina for controlling progression of myopia.

These and further features of the invention will be made apparent from the description of various examples and methodologies, described below by way of examples. In the description reference is made to the accompanying drawings which although diagrammatic, assist in explaining how the invention might be put into practice.

DETAILED DESCRIPTION OF THE EMBODIMENTS

In orthokeratology, typically a rigid gas permeable (RGP) contact lens is used to temporarily change the shape of the cornea in order to temporarily eliminate or reduce the refractive error of the eye. The RGP is placed on the eye either overnight or for a longer period (up to a few days) during the treatment period. At the end of the treatment period, the RGP lens is removed leaving the reshaped cornea to provide the necessary correction for the eye.

While the exact mechanism by which orthokeratology works is still being researched, it is known that the anterior corneal surface may increase or decrease in sagittal height and local curvature at various locations on the cornea depending on the method of treatment and the design of the orthokeratology lens.

This method thus provides the greatest flexibility in achieving the desired cornea profile for simultaneous refractive correction and reduction or elimination of progression of refractive error.

In soft contact lens orthokeratology, a soft (instead of RGP) contact lens is used to temporarily change the shape of the cornea in order to temporarily eliminate or reduce the refractive error of the eye. As in conventional orthokeratology, the lens is typically placed on the eye overnight during the treatment period. At the end of the treatment period, the lens is removed leaving the reshaped cornea to provide the necessary correction for the eye.

The aim of the present invention is to provide a method and associated orthokeratology device by which corneal reshaping can be achieved in such a way that the refractive error (i.e. the central refractive state) of the patient's eye can be corrected while simultaneously, the peripheral image (pertaining to the images of objects at wider field angles than the straight-ahead gaze direction) can be repositioned to be at least on the retina. This latter image repositioning provides the therapeutic stimulus for reducing or eliminating progression of myopia in the patient. For enhanced myopia therapy, the peripheral image may be placed in front of (i.e. in a direction from the retina towards the cornea) the retina. This introduces relative myopic defocus suitable for increasing the myopia therapy effect.

Figure 1:
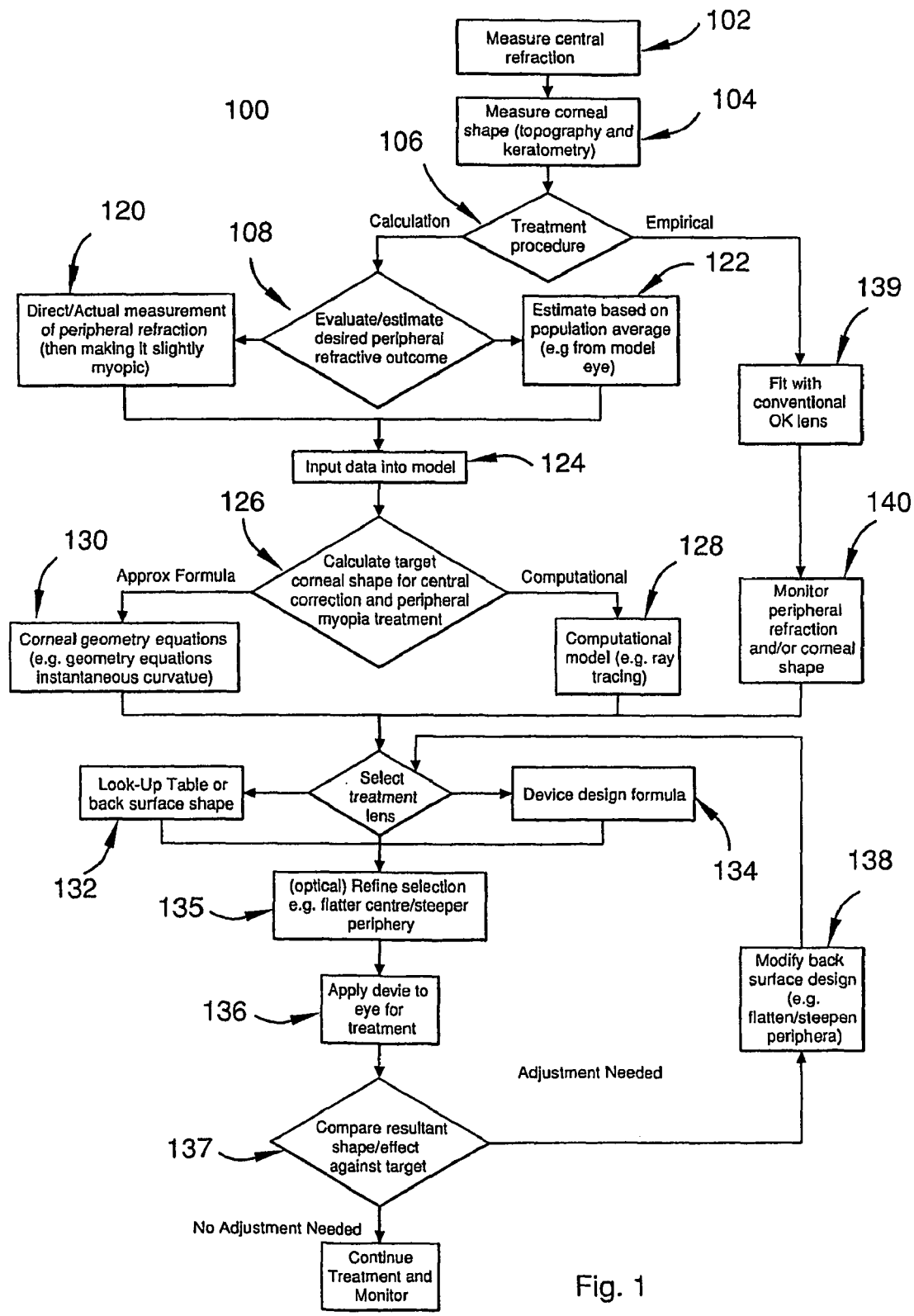
FIG. 1 shows a flowchart depicting the manner in which process of the invention is carried out.

The method of corneal reshaping according to the present invention entails the steps outlined in the flowchart 100 shown at FIG. 1.

First, the refractive error (i.e. central refractive state) of the eye is measured (102). This can be achieved using standard refraction instruments and techniques well known to ophthalmic practitioners.

Next, the corneal shape is quantified (104). This can be achieved using any of a number of corneal topography systems (e.g. videokeratograph) known to the ophthalmic practitioner.

The peripheral refractive state of the eye now needs to be established (106). This can be obtained by direct measurement with the same instruments and techniques as for central refraction with the additional step that the patient is instructed to gaze at an angle (the field angle) to the direction of the measurement instrument. Alternatively, typical values for a population (or subpopulation, e.g. myopes of particular amounts of myopia) from published sources may be used. Typically the refractive state of the eye is established at a pre-defined angle relative to the central eye axis. The peripheral angle is preferably selected to be between about 20° and about 45°, more typically between about 25° and 35°.

A treatment regime is now selected (108). It is preferred that a patient specific orthokeratology lens is fitted to the patient that will position the peripheral light focus anteriorly of the patient's retina in the manner described below, to thereby initiate myopia therapy. As mentioned, accurately establishing or estimating the shape of the eye is an important step in determining the shape of the post treatment cornea. Whilst it is important to seek to place the centrally focused image on the retina to ensure sharpness of central vision, it is careful control of the peripheral image that will facilitate myopia treatment.

Once the desired peripheral refraction outcome has been determined (110), the optimal correction to the peripheral corneal shape can either be determined by direct measurement (120) or may be established based on population averages (122).

The device for corneal reshaping is then applied to the eye using similar procedures to those of conventional corneal reshaping (orthokeratology) (118).

Once the pre-treatment shape of the eye has either been established or determined, the shape data is input (124) into a processor programmed with an algorithm as outlined below to calculate (126) the target shape of the lens to be fitted to the eye.

From these target design parameters, the final lens design is derived by taking into account additional factors including comfort, lens centration, and optimisation of mechanical effects on the cornea in order to achieve corneal reshaping.

In some cases, the final design may be intentionally varied (refined) according to known factors such as patient's history of rate of corneal reshaping and recovery (116).

Following the initial treatment, the patient's response may be monitored and the design of the corneal reshaping device adjusted to optimise the treatment effect.

Thus, the key aspects of the invention require an accurate pre-treatment evaluation of the shape and refractive error or the eye, both in the central region and the peripheral treatment zone. Using the data thus obtained or estimated, a lens is able to be designed which will correct for central refractive error, and treat the peripheral eye. These aspects are described in more detail below.

Computation of Key Design Parameter Values

As stated in the previous section, the aim of the present invention is to provide a method and associated device by which corneal reshaping can be achieved in such a way that the refractive error of the patient's eye can be corrected while simultaneously, the peripheral image can be repositioned to be on or in front of the retina.

In terms of optical design, correcting the central refractive state requires light from on-axis object points to be focussed to the central retina (i.e. towards the fovea). This is achieved, as in conventional corneal reshaping (or orthokeratology), by modifying the (central) radius of curvature of the cornea through application of the corneal reshaping device.

In order to reposition the peripheral image points, the reshaped cornea would need to have a peripheral shape that will focus light from the peripheral field angle onto the retina or in front of the retina. Thus, the radius of curvature at the peripheral cornea; the region that is responsible for focusing light from peripheral visual objects, needs to be altered to effect this. This is achieved in the present invention by the use of aspherically-shaped back surfaces on the cornea reshaping device. In some cases, this is further facilitated by the definition of two different zones under which corneal reshaping will be effected. The two zones are; the "central optical zone" that delivers the correct reshaping of the central cornea so as to bring about correct central vision correction similar to conventional orthokeratology; and the "peripheral therapeutic zone" that reshapes the peripheral cornea in order to bring about the appropriate change in peripheral refraction necessary to reposition the peripheral image onto or in front of the peripheral retina. The transition or boundary (or "junction" in the terminology of contact lens designers) between the central optical zone and the peripheral therapeutic zone may be blended with a smooth surface curve to improve smoothness of mechanical pressures on the cornea and comfort.

It is important to emphasise that while the lens designs for implementing elimination or retardation of myopia progression of this invention are describable using any of a number of geometrical coefficients for aspheric surfaces, the key feature that effects the repositioning of the peripheral image (i.e. peripheral refocusing) is the selection of the appropriate local radius of curvature over the region corresponding to the target peripheral field angle.

The following two methodologies can be employed to accurately establish the shape of the pre-treatment eye to thereby enable accurate determination of the shape of the treatment surface of the lens.

Method 1—Computer-Assisted Ray-Tracing Model

Figure 2:
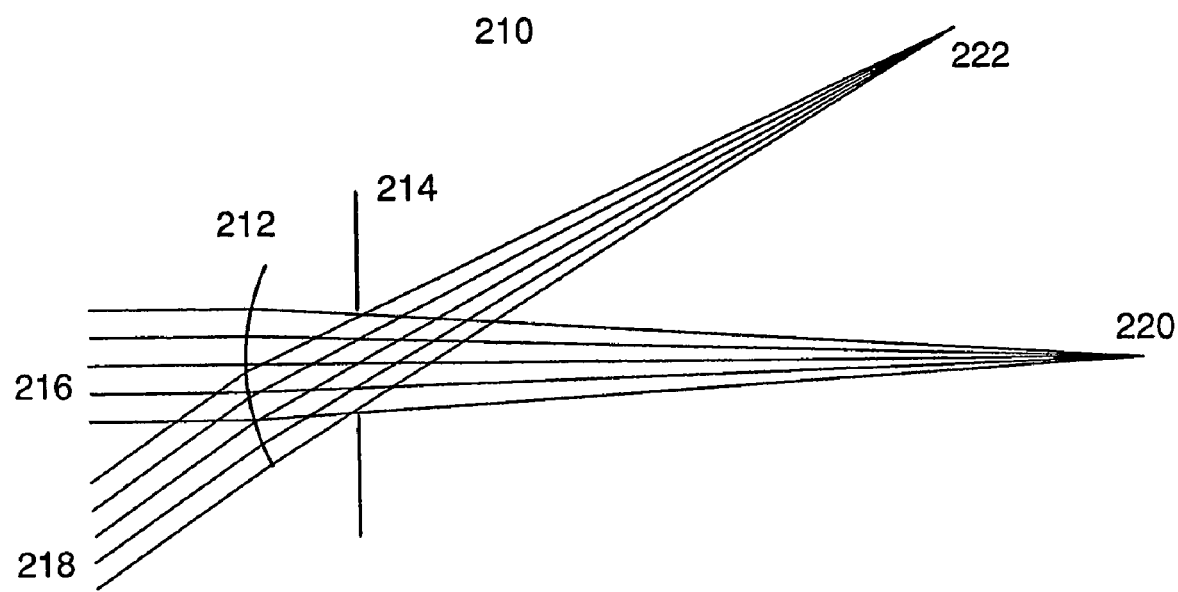
FIG. 2 shows diagrammatically the manner in which an eye is initially analysed using a computer assisted ray-tracing model.

In this method (box 128, FIG. 1), a computer program/software suitable for ray-tracing (e.g. such as commercially available software dedicated to optical ray-tracing or optical lens design) may be used. In FIG. 2 [Zemax diagram 1], an optical model 210 including an aspheric optical surface 212 describing the cornea and an aperture stop 214 representing the iris pupil of the eye is laid out. Using methods familiar to optical engineers and lens designers, two sets of rays representing light from a central (on-axis) object point 216, and light from a peripheral (off-axis) object point 218, are directed to the eye and configured to pass through the cornea 212 and on through the pupil 214 of the eye.

The surface 212 representing the cornea's anterior surface is given the appropriate parameters (e.g. conic equation including central radius and shape factor) for appropriate modelling of its optical behaviour. The values for these parameters may be obtained by direct measurement of corneal topography using a range of instruments and techniques such as a videokeratograph, which is a commercially available instrument commonly available in ophthalmic clinics. Alternatively, the values may be assumed from published population averages available from a large number of scientific publications.

As understood by optical engineers and lens designers, a merit function system is formulated (e.g. based on minimising the root-mean-square distribution of rays intersection with the image surface) to find, by an iterative optimisation process, the focal position for the central (on axis) rays 220 and the peripheral (off axis) rays 222. From these two focal positions 220 and 222, the central corneal front surface power $F_c$ and peripheral corneal front surface power $F_p$ can be obtained.

Figure 3:
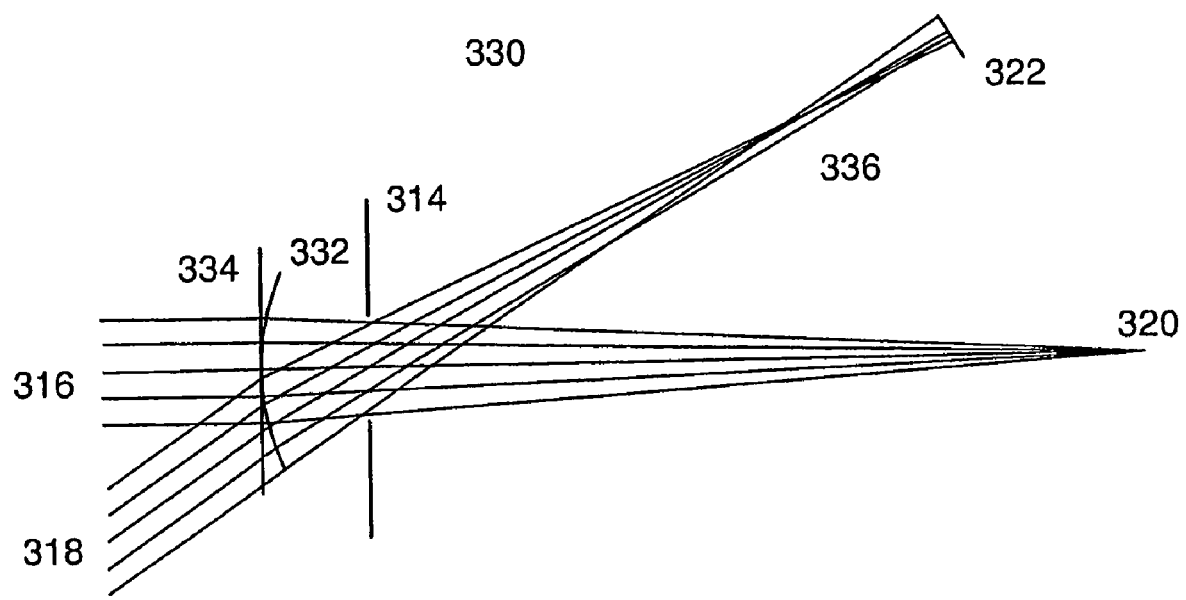
FIG. 3 shows a similar illustration to that of FIG. 2 of an eye in which the focus is modified by application of a lens to the front surface of the eye.

Next, the optical model and merit function system is modified using techniques familiar to lens designers and optical engineers (e.g. by the introduction of an additional surface having a refractive power equal and opposite to the refractive error). In FIG. 3, the starting optical system 210 of FIG. 2 has been modified to become the computational optical model 330. In this model 330, an additional surface 332 has been introduced. This surface 332 is configured in the ray-tracing program to represent the inverse of the central refractive state for light rays 316 from the on-axis/central object. That is, if the starting central refractive error to be corrected is A (e.g. −6 D), then the power of surface 334 will behave as −A (e.g. +6 D) to the central rays 316. In addition, surface 334 is configured to represent the sum of the inverse of the peripheral refractive state and the additional amount of peripheral refocusing targeted for the patient in order to reduce myopia progression. That is, if the starting peripheral refractive is B (e.g. −5 D) and the additional peripheral refocusing chosen is D (e.g. +0.5 D), then surface 332 will behave as −B−D (e.g. +5 D−0.5 D=+4.5 D) to peripheral rays 318. This modified optical system 330 is then re-optimised using a merit function system to bring the central 316 and peripheral 318 rays to focus on the original corneal surface focal positions 322 and 320. During this second optimisation, the shape of the cornea surface 332 is allowed to flex (e.g. by varying its radius of curvature, shape factor, etc). In this way, the ray-tracing software, during optimisation, will converge to a corneal surface 334 that will achieve correction of central refraction as well as repositioning the peripheral image points onto or in front of the retina. On completion of re-optimisation, the corneal surface 332 will represent the target corneal shape such that:

$F'_o$=(target post-treatment) central corneal power (in dioptres)=$F_o$+A $F'_p$=(target post-treatment) peripheral corneal power (in dioptres)=$F_p$+B+D Where A is the central refractive state of the eye (in dioptres), B is the peripheral refractive state of the eye (in dioptres), and D is the additional myopic defocus to incorporate for enhanced myopia therapy.

It is worth noting that, depending on the pupil size and the target field angle for designing the myopia progression therapy, that there may be regions on the target reshaped cornea 332 which is involved in focusing for both central 316 and peripheral light rays 318. Thus, the peripheral focus 322, following re-optimisation, will suffer from some amount of aberrations (as some peripheral light rays will not be able to provide an optimal peripheral focal image point). In FIG. 3, the aberration includes a type of radial astigmatism (a type of aberration) which is seen as a line focus at 336. However, provided the merit function system is constructed correctly, the 'most optimal' peripheral focus will still reside at 322 in the modified model 330.

It should be noted that the above method employing a ray-tracing model is illustrative. Many different approaches using ray-tracing/optical design programs may be used to arrive at similar specifications of the target reshaped cornea 332. For example, instead of making use of an 'idealised' optical surface 334 to represent central and peripheral refocusing, some software permits the use of specific merit function operands to direct the focal power of the target reshaped cornea surface 332. Thus, the exact approach can differ according to the software used and the exact approach to constructing a merit function system. The foregoing describes one method which now described, should provide the optical engineer and lens designers with sufficient guidance to construct his own ray-tracing model for computing the specifications for the reshaped corneal shape 932.

Field Angle to Select for Myopia Progression Therapy

Smith (U.S. Pat. No. 7,025,460) discusses methods for eliminating or retarding the progression of myopia by altering the peripheral refractive state (i.e. relative curvature of field) of an eye while simultaneously providing the appropriate correction of any central (on-axis) refractive error in order to provide good vision. Smith demonstrates that the peripheral retinal imagery is important and sufficient in directing the growth of the eye-ball, which is the primary way by which myopia comes about (elongation of the eye-ball). From this, it might be inferred that greater efficacy in myopia therapy can be achieved by introducing refocusing of the peripheral image points starting at lower peripheral field angles than starting at greater peripheral field angles. However, as explained above, depending on pupil size and target field angle, some region of the targeted reshaped cornea will be involved in focusing of both central and peripheral light rays. This results in a compromise of specification of the targeted reshaped cornea shape—needing to provide good central focus as well as providing correct refocusing of peripheral images—these two being conflicting requirements.

In practice, it is not necessary to ensure no overlap of central and peripheral lights rays on the reshaped cornea. A good compromise of the above contrasting requirements is to begin introducing peripheral refocusing the peripheral field angle that corresponds to the projection of the pupil margin (i.e. edge of the iris pupil) on to the reshaped cornea. For typical pupil sizes, this starting field angle of therapy is between 20° and 40°. With this configuration, approximately only half (or less) of the light rays from central and starting peripheral field angles would overlap.

EXAMPLE 1

Ray Tracing Method

In FIG. 2, an optical model as described above is laid out in a commercially-available software (Zemax, Zemax Inc) for optical design. The surface 212 representing the cornea is for a patient whose corneal shape was measured to be equivalent to a conics section with central radius of 7.70 mm and shape factor of 0.80. By optimisation for minimum RMS distribution of the light rays' intersection with the image surface at both the central and peripheral field angles, the focal positions associated with the central 220 and peripheral field 222 angles were found. These, by computation, were found to be equivalent to a central corneal power of $F_c$=49.0 D and a peripheral corneal power at 350 of $F_p$=54.1 D.

For this example, suppose the patient's central and peripheral refractive state were found to be A=−6.00 D and B=−5.00 D. Further, supporting it was desired to provide an enhanced myopia therapy by introducing an additional amount of myopic defocus to the periphery of 0.50 D. In order to compute the target reshaped corneal surface 332 that would achieve best correction for both central and peripheral image, an ideal refracting surface 334 (e.g. paraxial surface) was placed at the same position as the anterior cornea. This ideal refracting surface 334 is configured to behave as a +6.00 D (=−A) for central rays and +4.50 D (=−B−D) for peripheral rays.

Keeping the focal positions 320 and 322 as found from the first optimisation, a second optimisation is initiated. Following this second optimisation, during which the target reshaped cornea 332 is assumed to be a surface described by a conic section, the central radius and shape factor of the target reshaped cornea 332 are allowed to vary to achieve the best correction (i.e. minimise RMS distribution of ray intersection with the image surface), the shape of the target (reshaped) cornea 332 is found.

A conic section is a geometrical shape family including circles, ellipses, parabolas and hyperbolas. It is a particularly favoured geometrical method for describing aspheric surfaces in contact lens design as there are few parameters involved in the unique description of a given conic section. These parameters are the central radius of curvature ($r_o$) and shape factor (p, or p value). (Note that often, instead of the shape factor, p, eccentricity, e, or conic constant k or q may be used. However, these factors, p, e, k or q relates directly with one another mathematically in precise way and so do not produce distinct surfaces through their use). In conic sections, the central radius, $r_o$, describes the 'instantaneous' radius of curvature at the very apex (or "vertex") of the surface. In the idealised cornea, this is the radius at the central 'tip' of the cornea. The shape factor, p, describes how the shape departs from a circle; a p value of 1 represents a circle, p=0 is a parabola, p between 0 and 1 is an ellipse as is p greater than 1, while a negative p value denotes a hyperbola. For the purpose of this specification, it is important to distinguish between two types of ellipses; where p is less than 1 and p is greater than 1. In the former ($0 \leq p \leq 1$), the ellipse is said to be "prolate" or a flattening ellipse. In a flattening ellipse, the focusing power of surface decreases away from the apex/tip. In the latter (p>1), the ellipse is said to be "oblate" or a steepening ellipse. In such ellipses, the focusing power increases (shorter focal length, greater dioptric value) away from the apex/tip.

In this example, the specification of the target reshaped corneal surface described as a conic section are $r'_o$ (target central radius)=8.774 mm and p' (target shape factor)=2.286 indicating a steepening elliptical shape.

It can now be seen that by following the above method, the target shape for the anterior cornea can be obtained for any individual values for central refraction, peripheral refraction, additional peripheral myopic defocus and corneal shape.

It is important to emphasise here that the appropriate amount of peripheral refocusing (i.e. repositioning of the peripheral image point) is achieved by computing and selecting the local radius of curvature of the target reshaped corneal surface at the region associated with the peripheral light rays. However, in order to translate these central and peripheral local radii of curvature specifications into a lens design, these radii are typically summarised into an aspheric surface that possesses these radii at the respective location on the surface.

For convenience, ophthalmic practitioners have conventionally described the cornea as a conic section. Hence, throughout this specification, conic sections have been used. However, this is only by way of illustration as it can now be seen that the above method is not limited to describing the target (post-treatment, reshaped) corneal shape as a conic section. The initial and/or target corneal shape may be described using more general aspheric descriptions including but not limited to polynomials, splines, Fourier synthesis, etc, as understood by applied mathematicians, optical engineers and lens designers.

For example, in the above Example 1, when re-optimised using an $8_{th}$-order even polynomial (i.e. a polynomial that includes only the even powers up to $8^{th}$ order) added to a basic spherical surface, to describe the target cornea, returns a surface description in which the basic spherical surface has radius=8.774 mm; and the additional polynomial surface altitude or height $y = a_2 \cdot x^2 + a_4 \cdot x^4 + a_6 \cdot x^6 + a_8 \cdot x^8$ in which y is the surface height (in millimeter) of the surface which is added to the basic spherical surface defined by the radius for any given surface point located at distance x from the axis; $a_2 = 3.813 \times 10^{-3}$, $a_4 = -1.354 \times 10^{-3}$, $a_6 = 3.368 \times 10^{-4}$ and $a_8 = -1.826 \times 10^{-5}$.

The design parameter values can now be used to calculate the final design for the corneal reshaping device. This will be described in a later section.

Method 2—Approximate Equation

While computation of the required design parameter values for the device is most precisely achieved by employing a ray-tracing model as described above, there are occasions when computer and/or software for ray-tracing may not be available. In such cases, it is possible to estimate (box 130, FIG. 1) approximately, but nevertheless with sufficient accuracy for efficacy, starting values for these design parameters by applying the system of equations detailed here. By employing these equations, using e.g. a hand-held calculator, good starting values for design parameters of the current device can be derived.

Given values for:
A=central refractive state (in dioptres),
B=peripheral refractive state (in dioptres),
D=amount of additional myopic defocus to induce in the periphery for enhanced myopia therapy (in dioptres),
$r_o$=(initial, pre-treatment) central radius of curvature of the cornea (in millimeter),
p=(initial, pre-treatment) shape factor of curvature of the cornea, and
θ=field angle at which peripheral refraction (B) is measured and myopia therapy defocus (D) is to be applied (in degrees).

These values may be obtained by direct measurement using a range of clinical instruments and techniques known to ophthalmic practitioners, or assumed according to average values for the population (available from a number of published scientific articles).

Parameters relating to the initial (pre-treatment) state can first be calculated as:

$x$=approximate ray-height (in millimeter)=θ·π/60

$r_s$=(initial) sagittal radius of the cornea (in millimeter)= $r_o^2 + (1-p) \cdot x^2$ $r_t$=(initial) tangential radius of the cornea (in millimeter)=$r_s^3/r_o^2$ $F_c$=(initial) central corneal power (in dioptres)=1000· $(n-1)/r_o$ $F_p$=(initial) peripheral corneal power (in dioptres)= 2000·(n−1)/($r_s+r_t$)

Where n is the refractive index of the cornea which, according to scientific publications, is typically about 1.375.

Good approximations for the design parameter values can be calculated as follows:

$F'_o$=(target post-treatment) central corneal power (in dioptres)=$F_o+A$ $F'_p$=(target post-treatment) peripheral corneal power (in dioptres)=$F_p+A+Z·(B-A+D)$ $F'_s$=(target post-treatment) sagittal corneal power (in dioptres)=$F'_o+(F'_p-F'_o)/2$ Note that Z is a pupillary zone compensation factor. Research has shown that empirically assigning a value of about 3 to this factor gives a good approximation to the design parameter values. However, this factor is related to the pupil and zone size of the patient and device respectively. For smaller or larger pupils or zone sizes, a smaller or larger (respectively) value for Z can be adopted for better approximation.

Finally, the central radius and shape factor for the device may be calculated as:

$r'_o$=design value for central radius of curvature of back surface of device (in millimeter)=$1000 \cdot (n-1)/F'_o$ $r'_s$=design value for sagittal radius of curvature of back surface of device (in millimeter)=$1000 \cdot (n-1)/F'_s$ $p'$=design shape factor for back surface of device=$1+(r'^2_o-(r'^2_o-(r'_s \cdot r'^2_o)^{2/3})/x^2$ Translation of Key Design Parameters to Final Lens Design Having calculated (following the methods described in the previous section) the key design parameters that governs correction of central refractive error while simultaneously repositions the peripheral image onto or in front of the peripheral retina, these parameters are now combined with secondary design features to complete the final design for the lens.

The considerations in arriving at the final design encompasses the principles of achieving centration of the device with respect to the cornea/eye, applying the appropriate mechanical effect on the cornea in order to reshape the cornea in the most efficient and efficacious manner, as well as providing acceptable to good comfort throughout the wearing/ treatment period. Optionally a lens of known back surface shape may be selected (box 132, FIG. 1) but preferably a patient specific lens is designed (box 134, FIG. 1) in the following manner.

In summary, the following inputs are required prior to initiating the lens design:

Subject flat k reading
Subject flat k eccentricity (e or p) ($p=1-e^2$)
Subject refractive error
Computed Base Curve (BC) $R_o$ & p for MC
Lens material properties RI, Dk
Lens dimension preferences (CT, Dia, ET, OZw, minimum and maximum thickness constraints)
Computer controlled lathe designed to accept meridional input in terms of x,z coordinates.

Figure 4A:
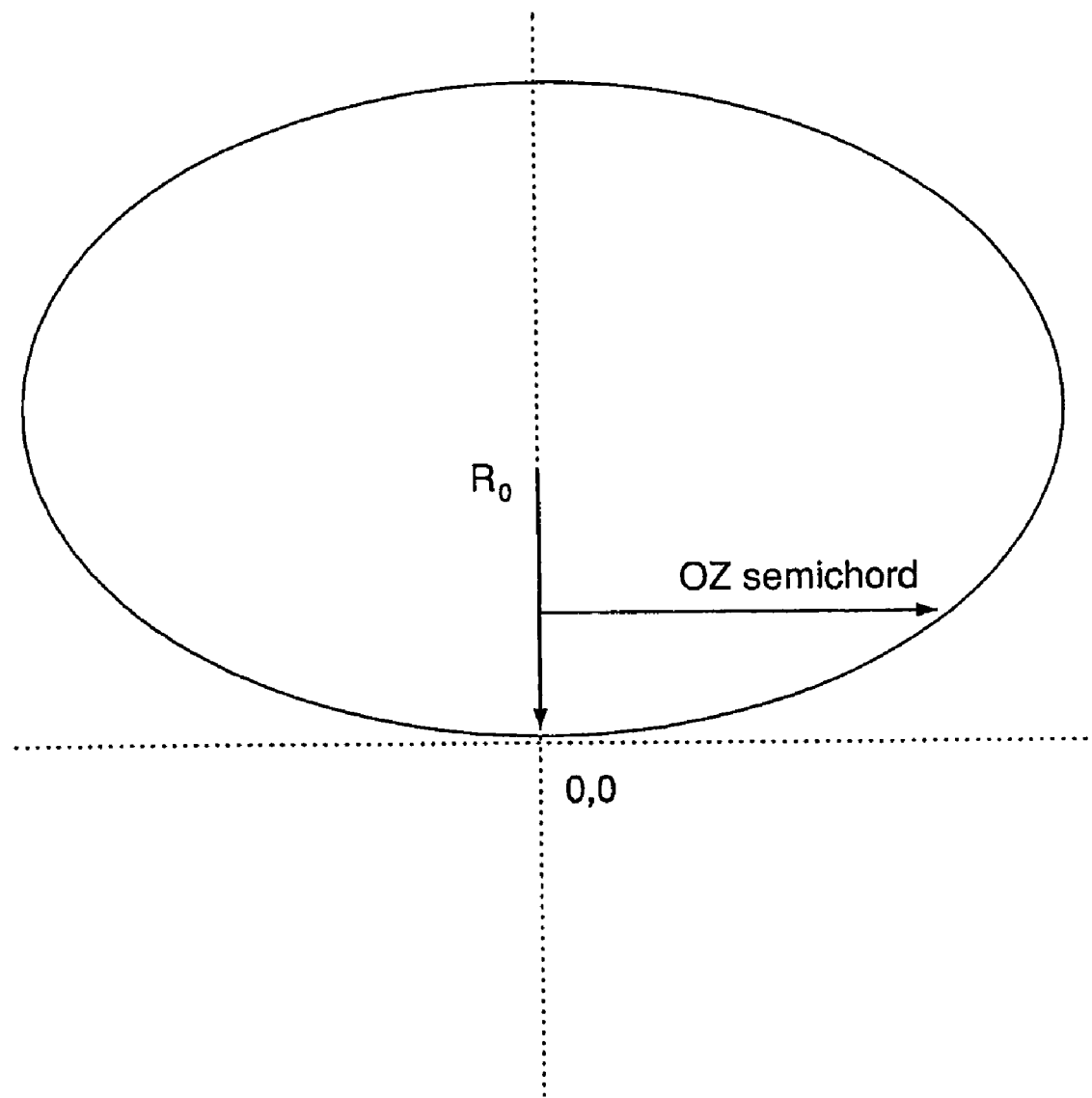
FIGS. 4a to 4q show the steps to be followed in producing a lens, once the design parameters have been determined.

Steps to be followed:

Step 1: See FIG. 4a.

The Base Curve (BC, $R_1$) coordinates are computed. The $R_0$ and P from the MC model in a conic section are used. The apex of the curve (402) is placed at position 0, $0_1$, and R0 origin is placed on the +z axis.

Figure 4B:
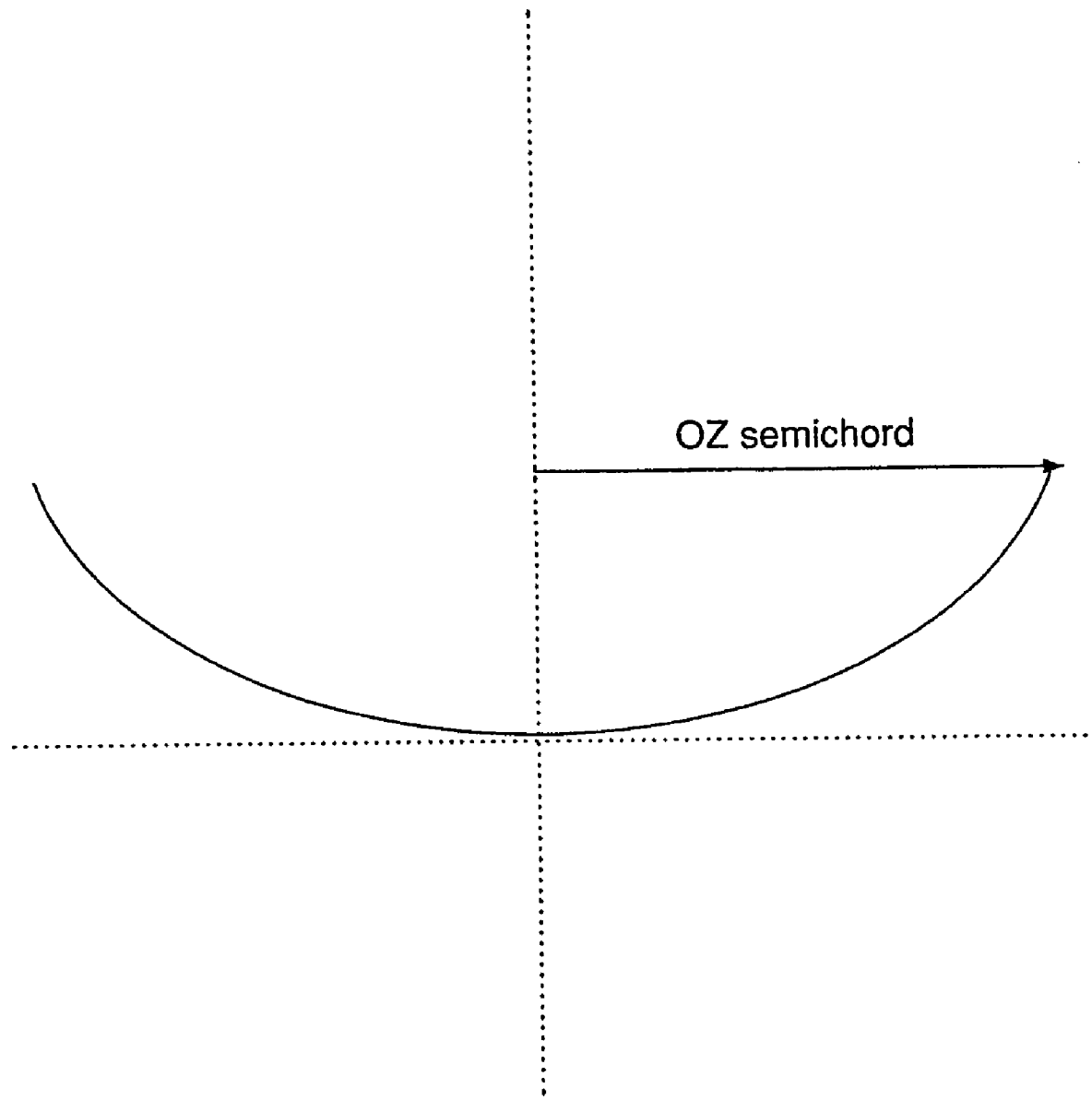

Step 2: See FIG. 4b.

The sagittal depth of the required Base Curve is computed at small intervals (~5μ) from central axis to the semi-chord of the Optical Zone (typically half the subject's normal pupil diameter).

Figure 4C:
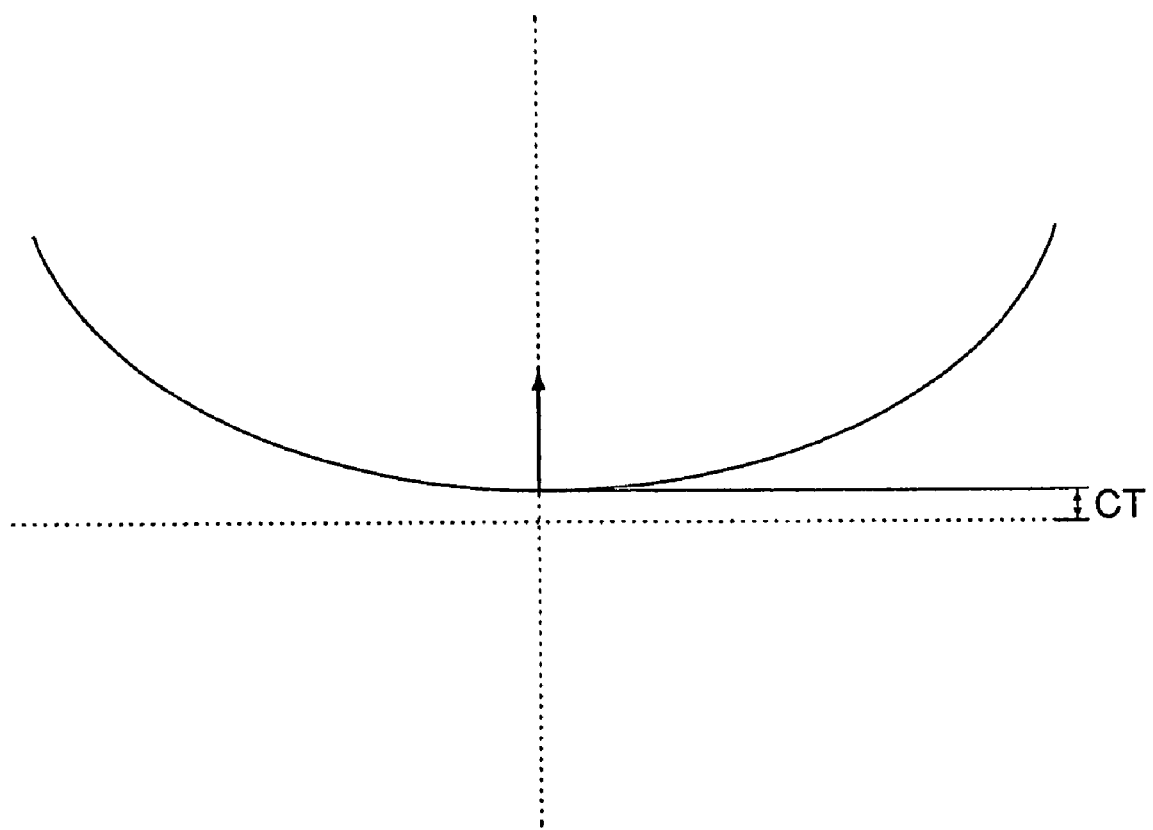

Step 3: See FIG. 4c.

All sagittal Base Curve points are increased by an increment of the lens centre thickness (CT).

Step 4: See FIG. 4d.

The alignment curve (AC) is computed.

Figure 4D:
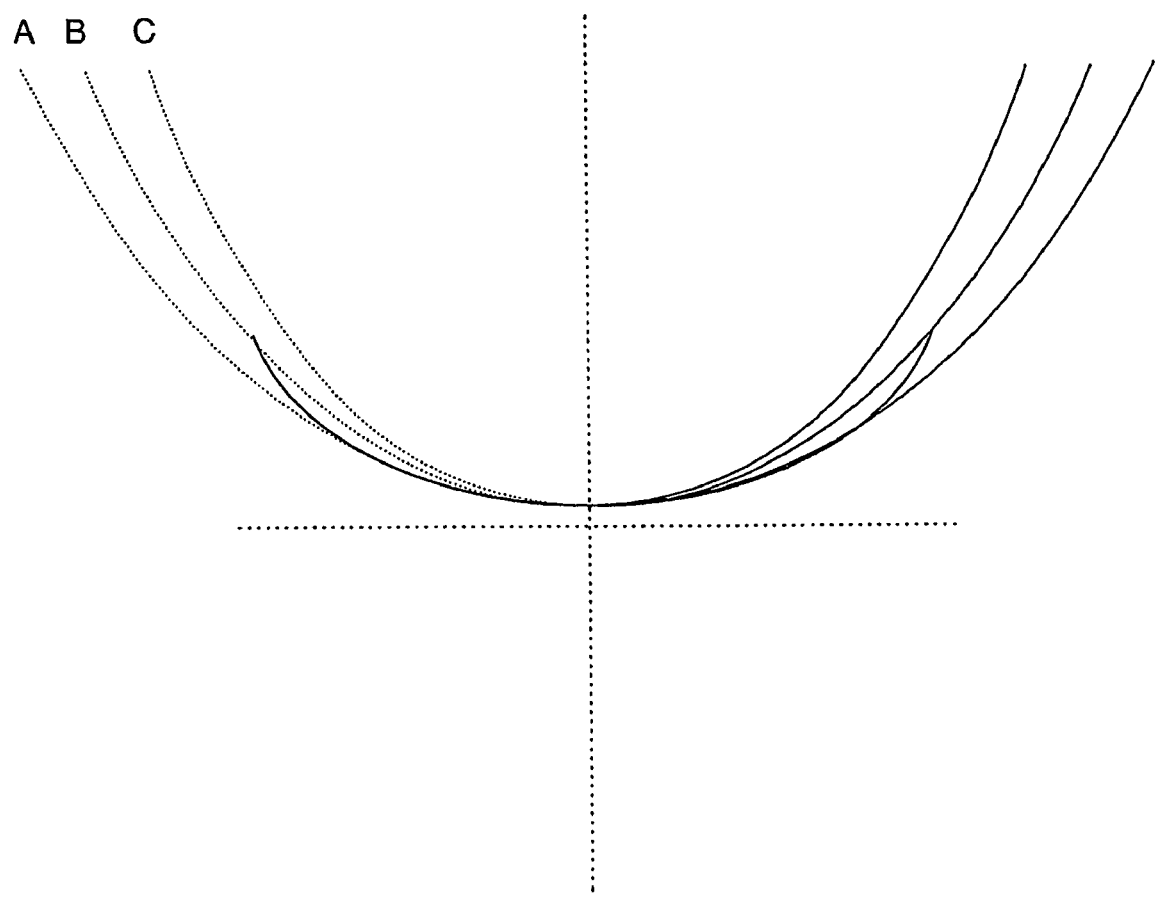

Compute at equivalent small intervals the sagittal depth of the modeled subject cornea using flat k (converted to a radius) and eccentricity if available over full diameter of the lens using same orientation and coordinate system as employed for BC. Three Corneal relationships are depicted in FIG. 4d. Corneas relationships A and B can be fitted with a single oblate curve without need for a flatter central zone. Cornea relationship C is dealt with in the two zone concentric OZ.

Figure 4E:
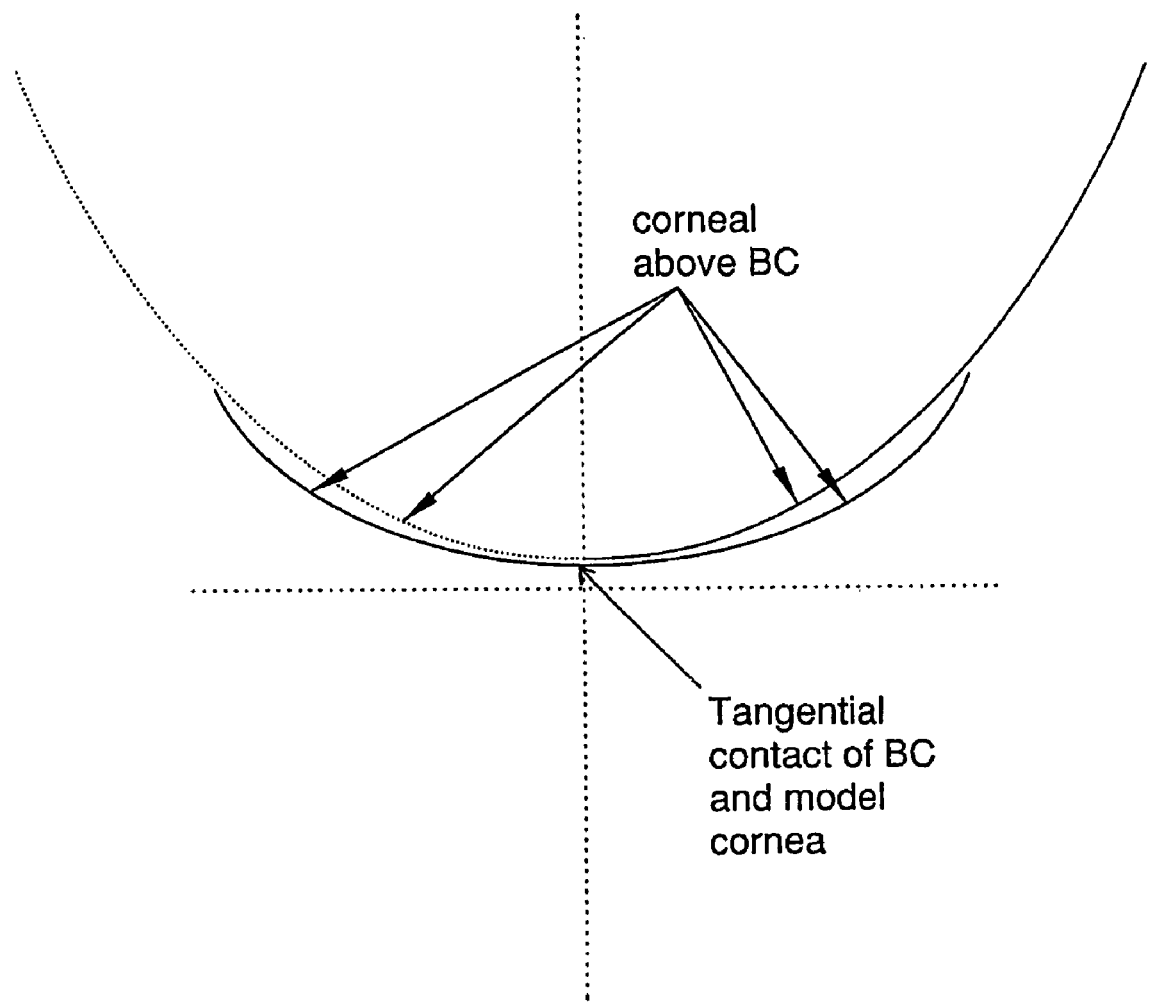

Step 5: See FIG. 4e.

Adjust (visually on chart or mathematically) the origin for corneal sagittal computations (green dotted line) to allow tangential contact of cornea to BC at location where all other corneal points are above (greater Z) than BC.

Figure 4F:
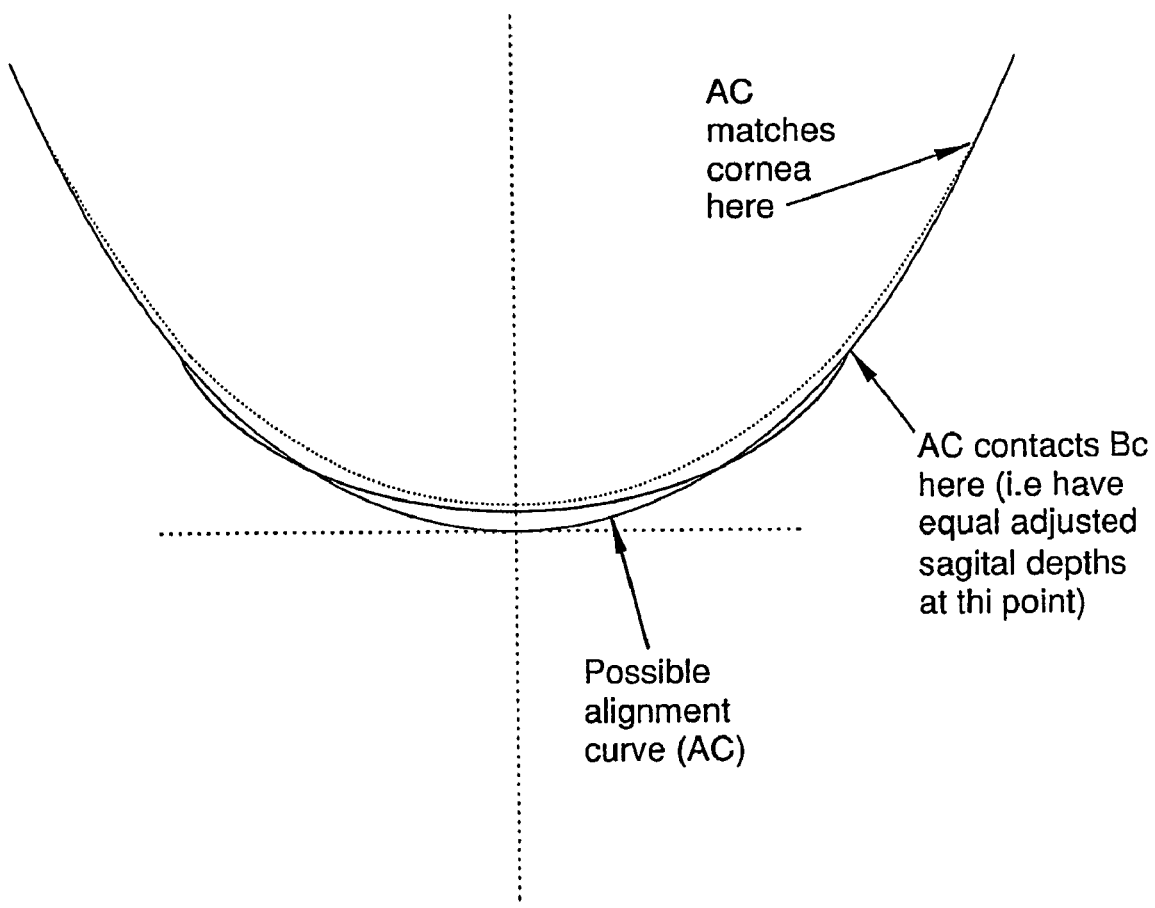

Step 6: See FIG. 4f.

The adjusted corneal points (ACP's) may be used as a guide in selecting improved AC parameters to achieve optimum fit.

Compute sagittal points for alignment curve (concentric to OZ) starting with spherical radius in the range of 1 D flatter to 1 D steeper than subject's flat k.

Adjust origin of the alignment curve (AC) such that its sagittal depth at the semi-chard of OZ equals that of the BC at that same meridional location.

Figure 4G:
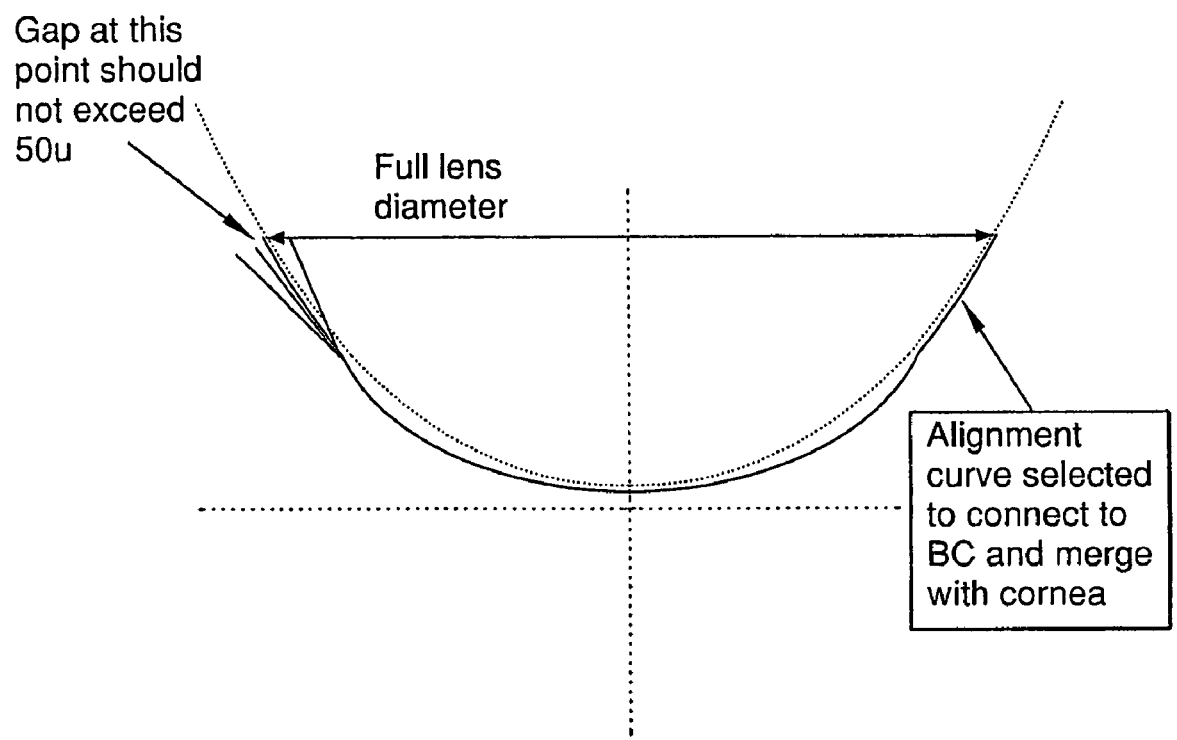

Step 7: See FIG. 4g.

Compare the sagittal depth of the AC and the adjusted subject cornea (ACPs) at the full diameter of the lens.

While maintaining the equivalence of the sagittal depth of AC and BC at the OZ diameter (by adjusting AC origin as needed) vary the radius and/or shape factor of the AC to bring the AC into near alignment with the ACPs such that at the full diameter the lens and cornea deviate by less than 50μ.

Figure 4H:
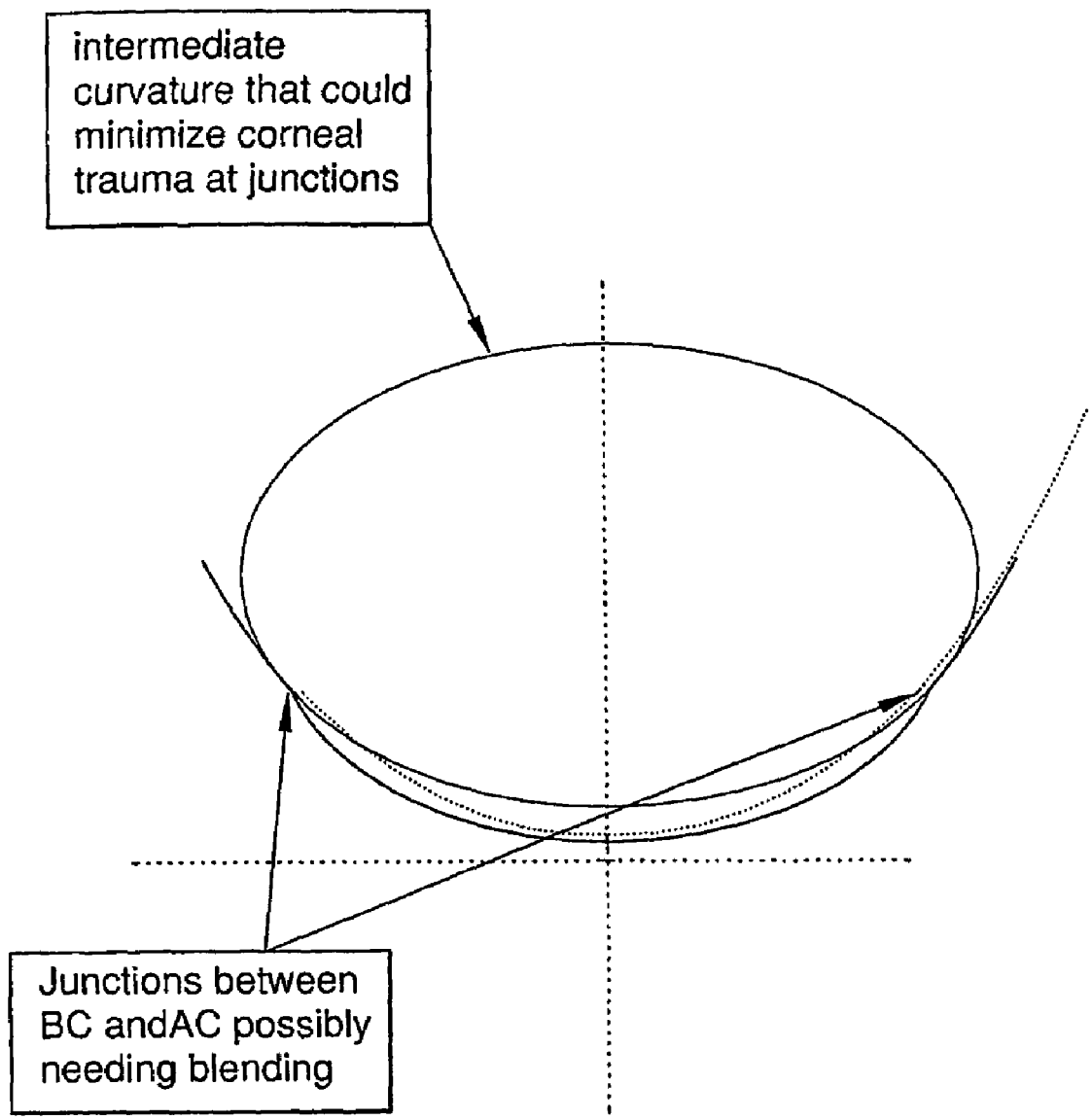

Step 8: See FIG. 4h

Blend Junctions.

At the location of any posterior junction, one or more alternate curvatures (of relatively narrow width) may be inserted mathematically at posterior junctions or mechanically after fabrication to smooth such junctions to avoid excessive corneal compression over small corneal areas.

Figure 4I:
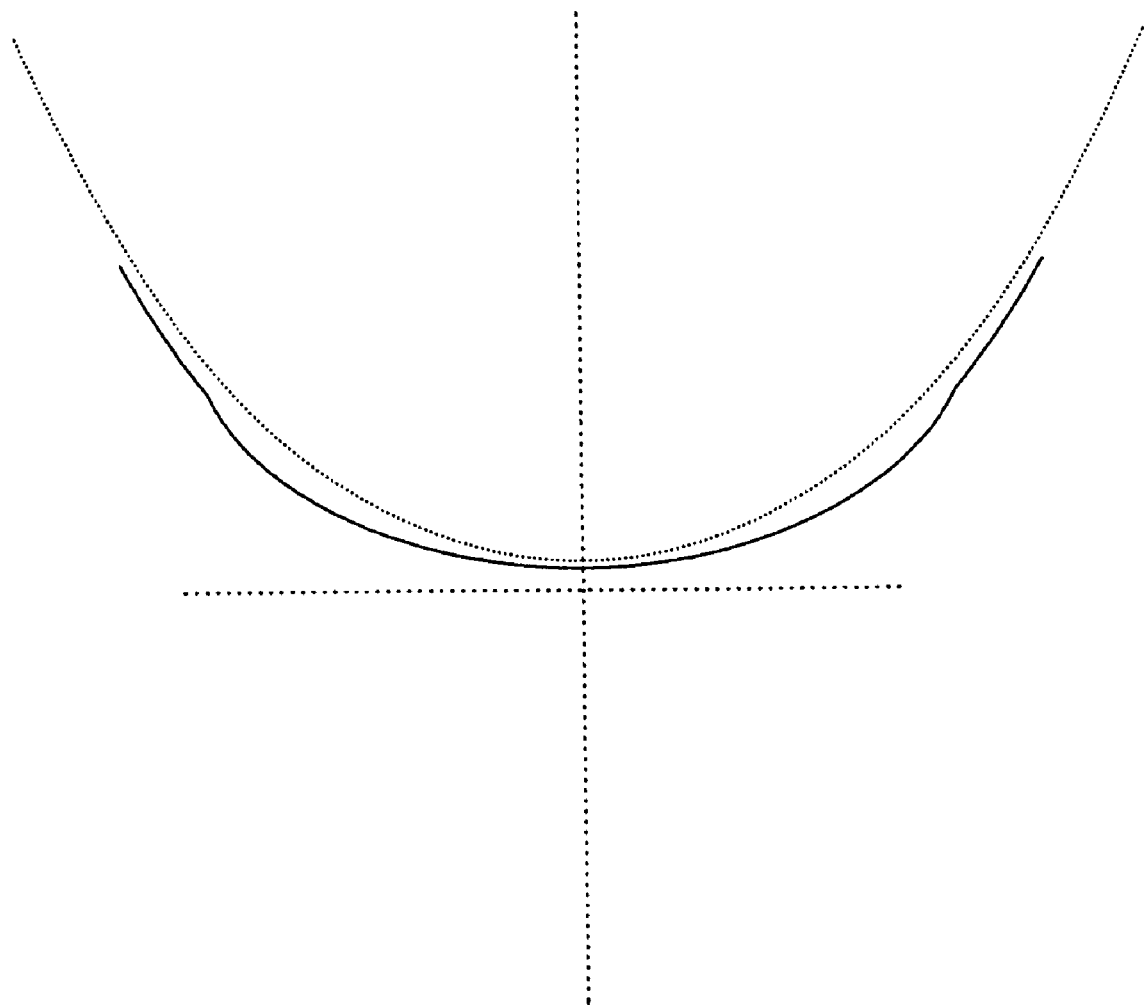

A depiction of the blended Base Curve is shown in FIG. 4i.

Figure 4J:
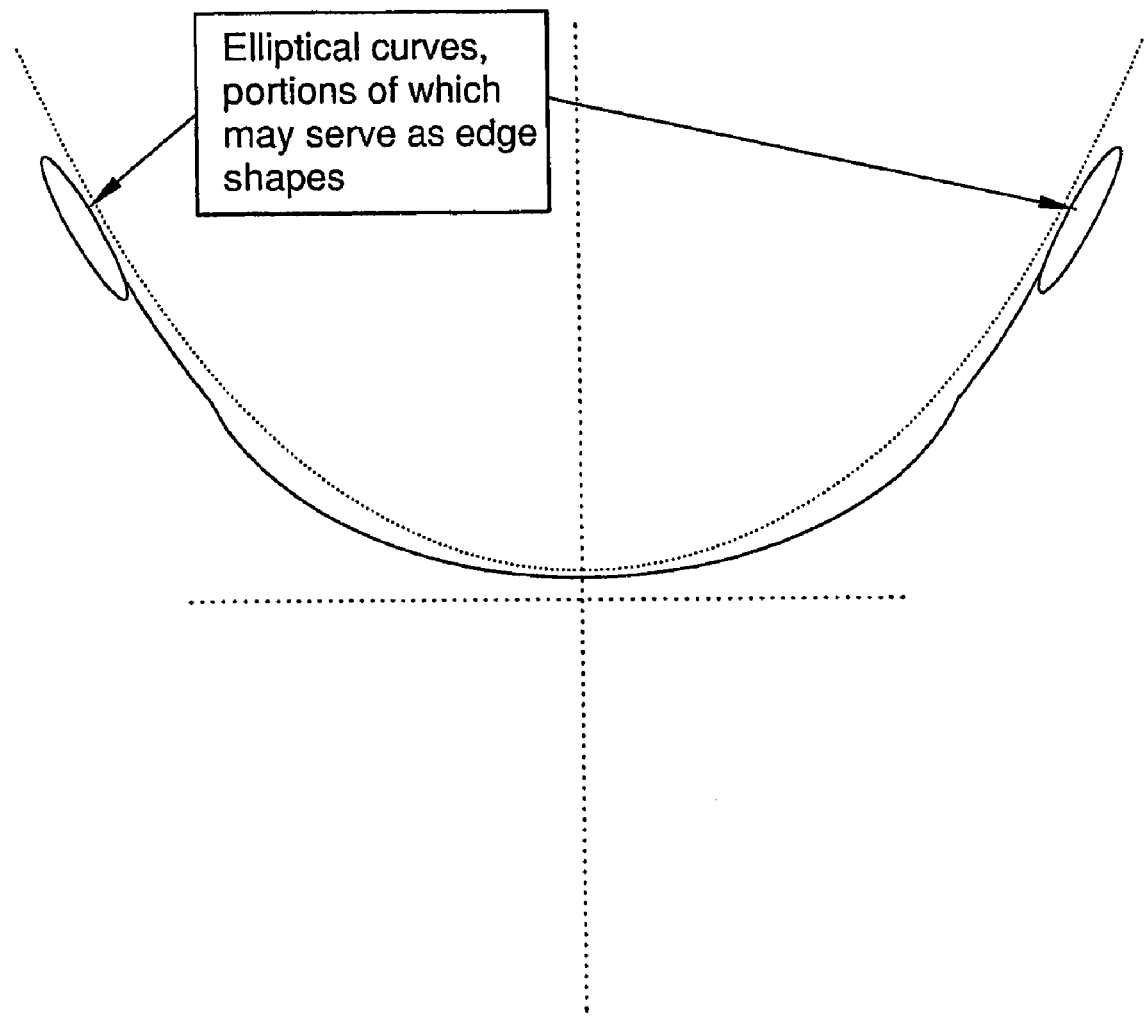
Figure 4K:
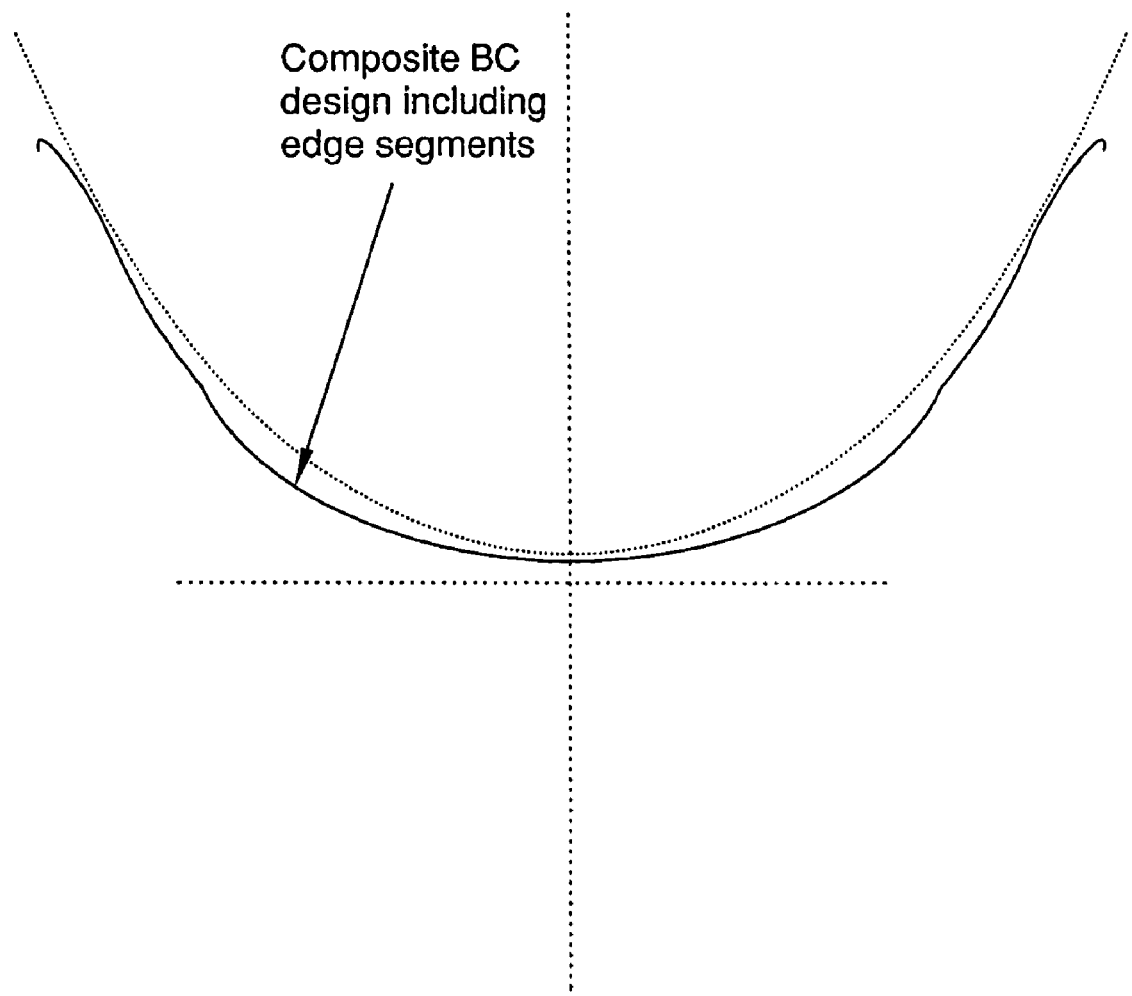
Figure 4I:
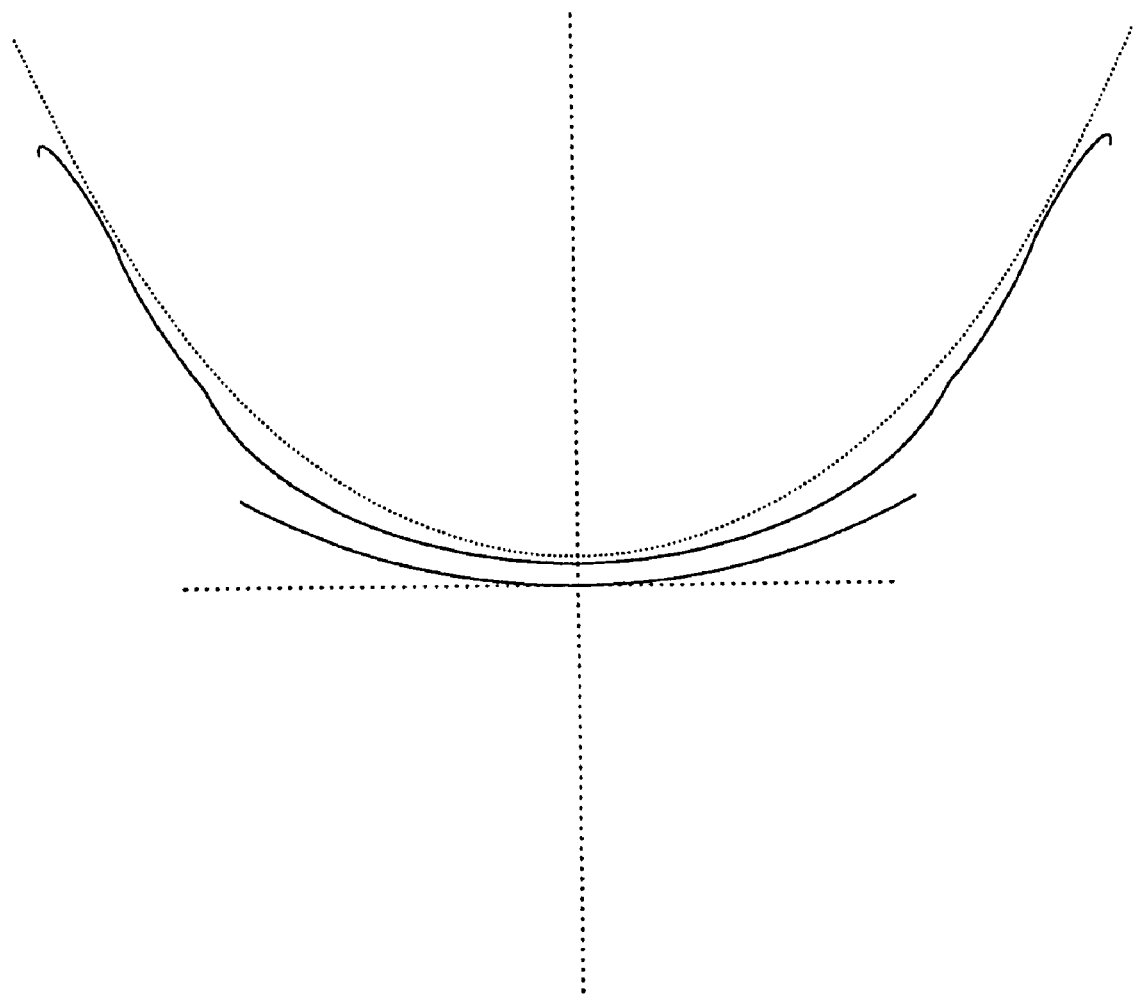

Step 9: See FIG. 4j and FIG. 4k.

The edge of the lens is then determined by techniques well known to those skilled in the art, and the x, y coordinates of the selected Base Curve segments are combined to create a continuous series of points from centre to lens edge to generate a final composite Base Curve description.

Step 10: See FIG. 4l

The front curve (FC) is now designed.

Using the BC $R_0$, the lens CT and lens material properties, compute the radius of a front Curve (FC) that will yield plano (or other desired power such as "overshoot") optical power on the central axis.

Placing the apex on the front curve at 0,0 and its origin on the z axis, compare point by point the axial distance between points of the composite BC.

Figure 4M:
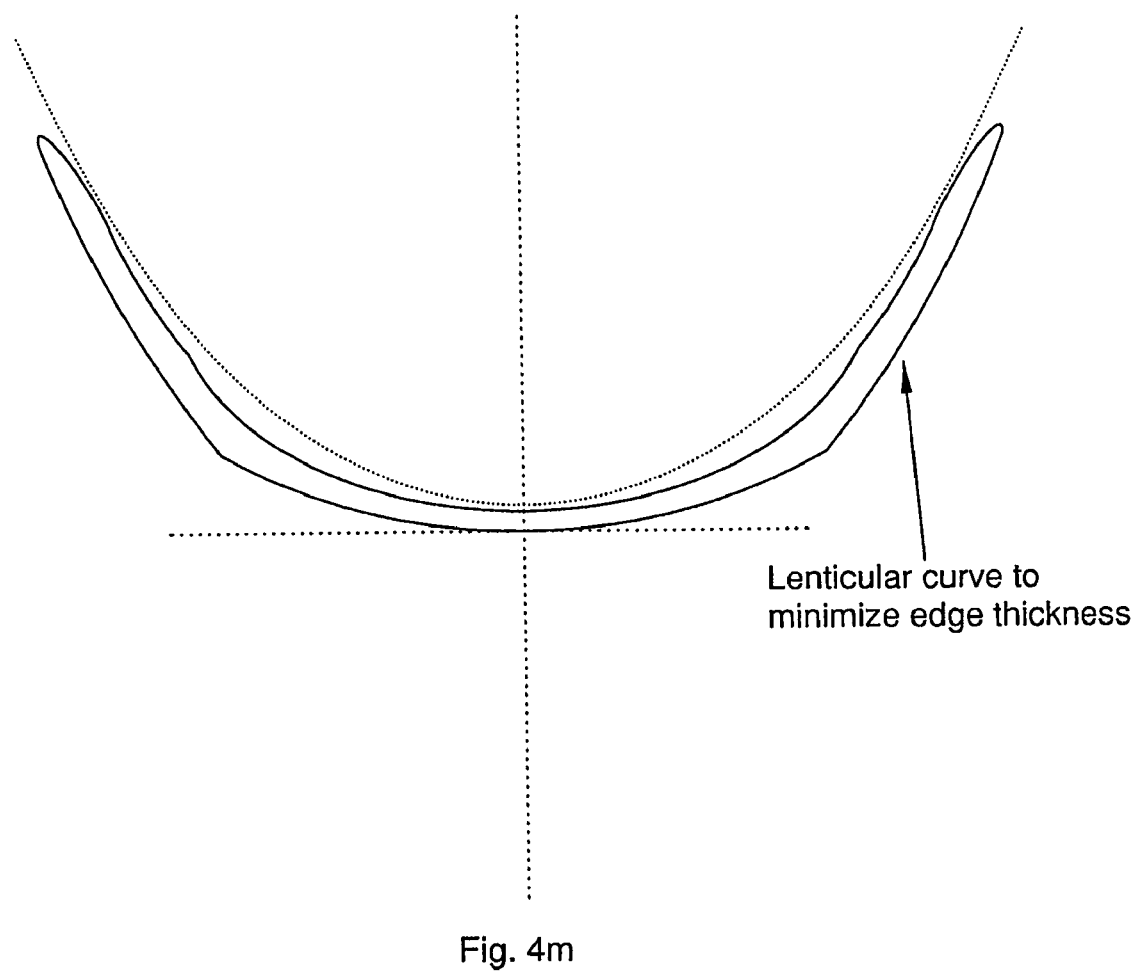

Step 11: See FIG. 4m.

Determine if any points on the FC and final BC are either too close or too distant (as understood by those skilled in the art) and if necessary include one or more "lenticular" curvatures in a composite FC.

Figure 4N:
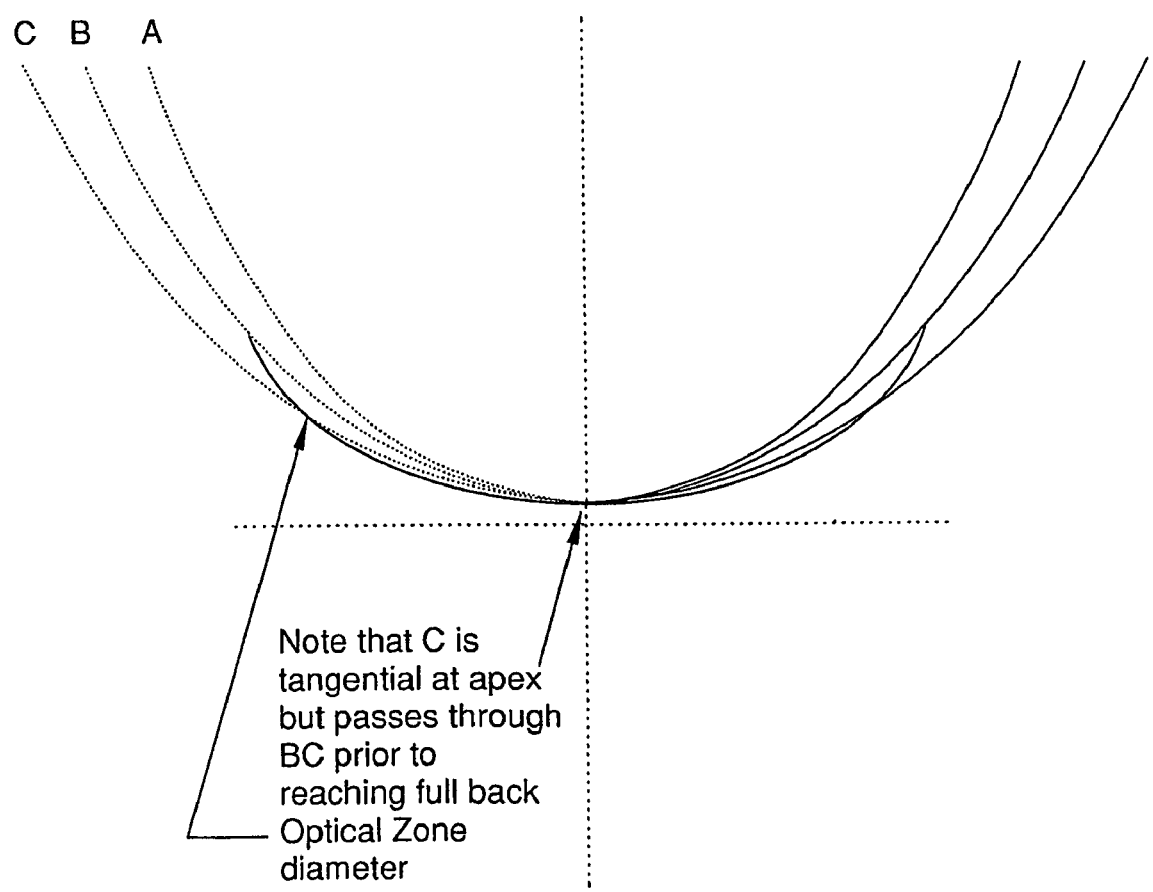

Step 12: See FIG. 4n.

In circumstances where the model predicts an oblate curvature resulting in a BC/cornea relationship such as in C, it may be necessary to include a second zone in black optic zone to reduce the sagittal depth of the BC at the OZ semi chord.

Figure 4O:
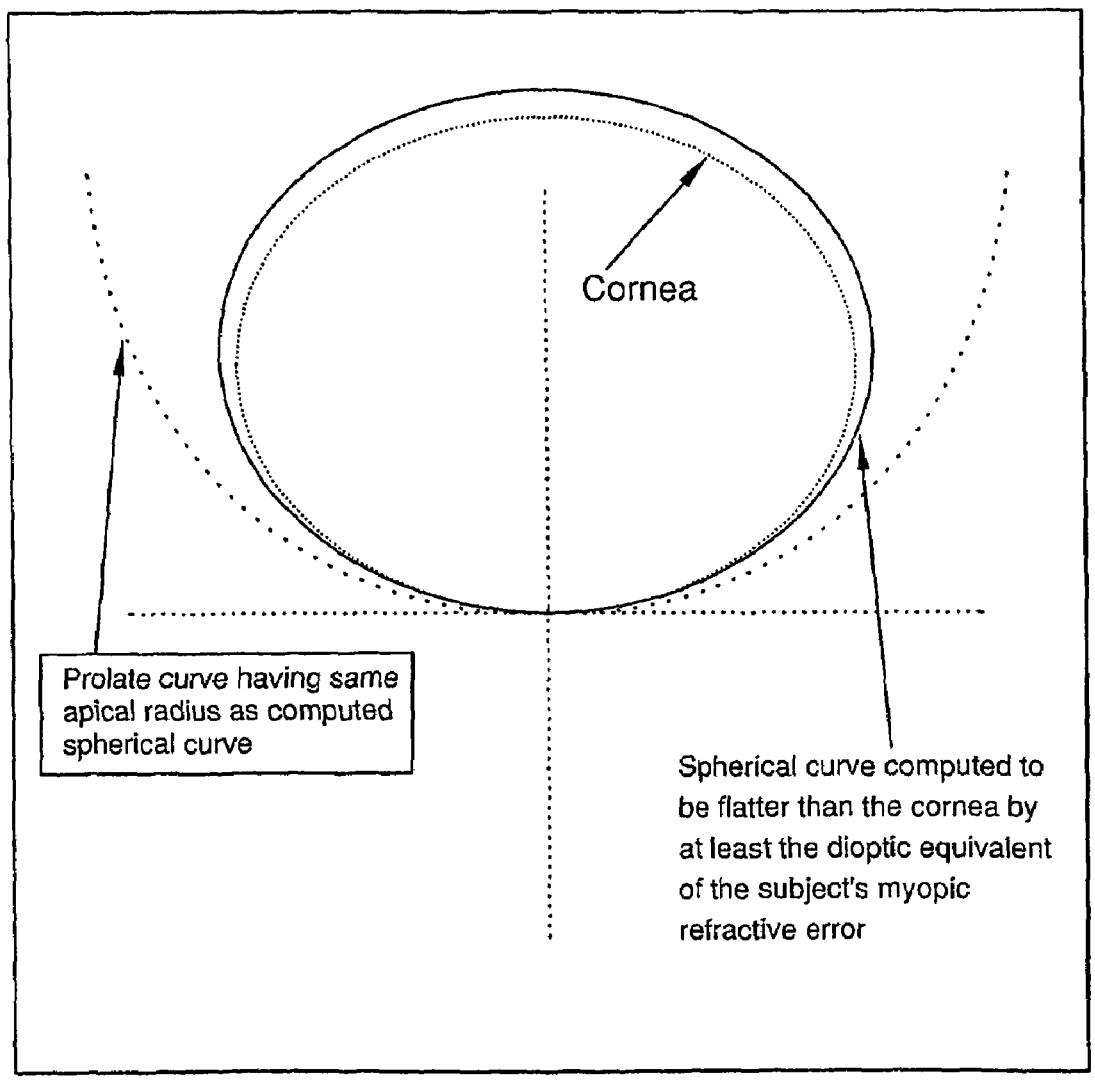
Figure 4P:
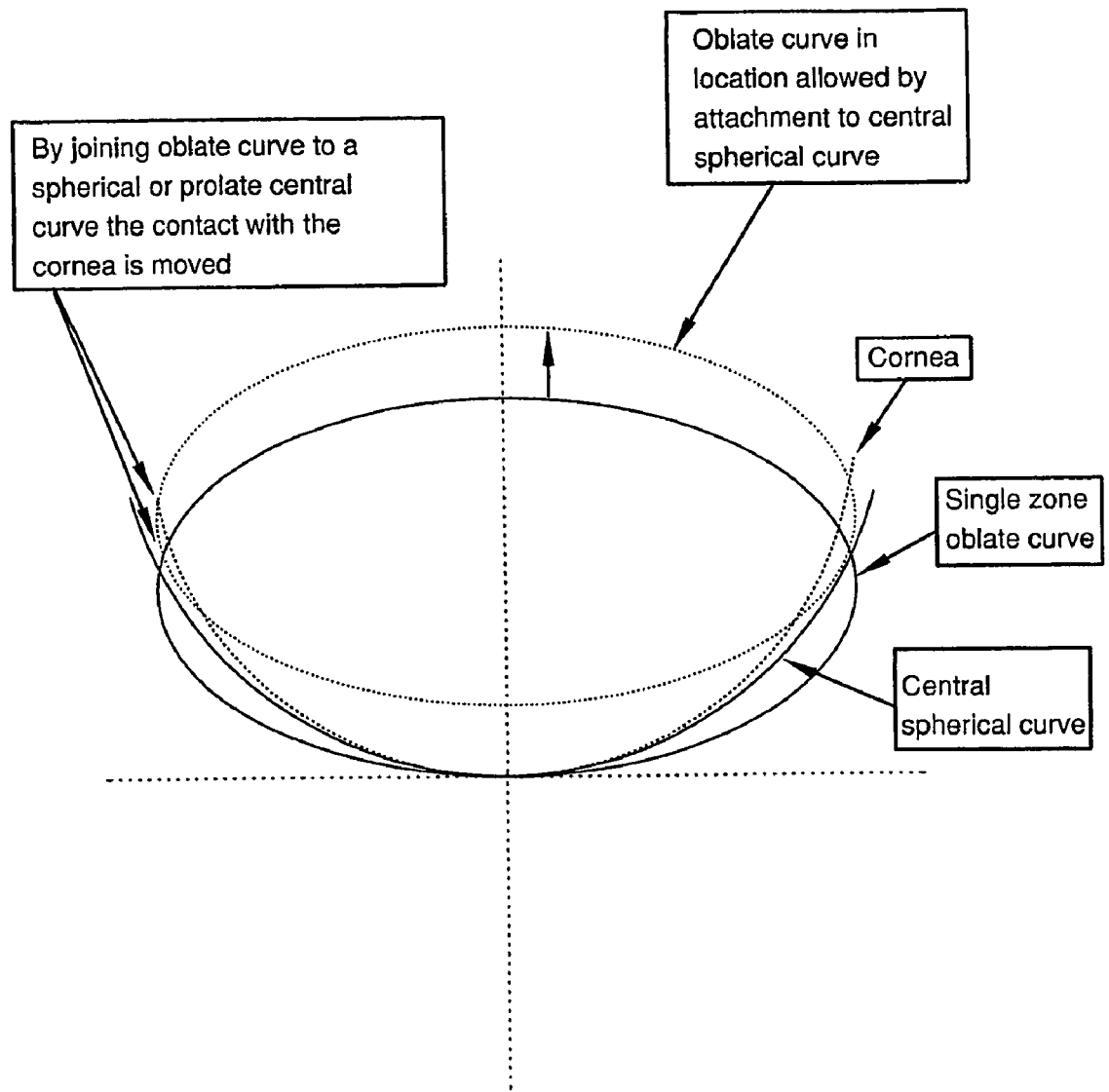
Figure 4Q:
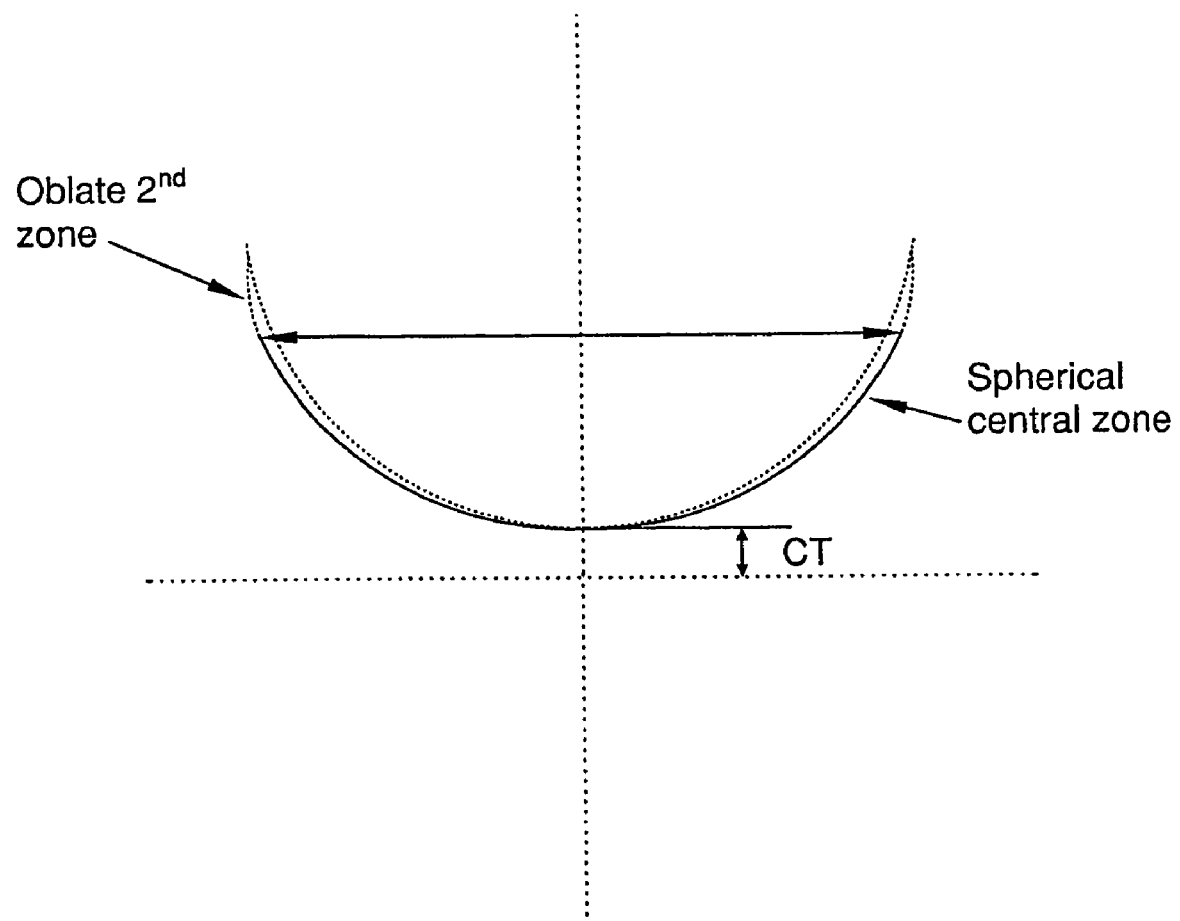

Step 13: See FIG. 4o.

Compute radius for central OZ ($R_{1a}$).

The OZ of this lens comprises 2 curves, a central curve $R_{1a}$ and a concentric zone of different curvature $R_{1b}$. Subtract subject's refractive error (in diopters) from the subjects flat k reading.

Further subtract any desired "overshoot" from the above result.

Convert diopteric result to radius using RI of the cornea.

Compute Central Base Curve ($R_{1a}$) Coordinates.

Using computed central OZ radius $R_{1a}$ as $R_0$, one may elect to adjust this spherical curvature to asphere by including a slight flattening (typically $p \leq 0.6$) as suggested by the subject's measured eccentricity.

Definition of Zones And A Multizone Lens

It should be noted that since the objective is to achieve correction of the central refractive error while simultaneously repositioning the peripheral image point, the region of the lens may be considered as two zones. In such a design definition, the centrally placed zone is configured with the appropriate back surface radius of curvature to achieve correction of central refractive error. Surrounding this central zone is the more peripheral therapeutic zone configured with the appropriate back surface radius of curvature to reposition the peripheral image onto or in front of the retina. The appropriate radii of the two zones may be computed following the steps and methods described previously. However, the benefits in defining and considering the design as two key zones may be described as follows.

When a lens is designed for corneal reshaping (i.e. orthokeratology), the central back surface is typically so flat (i.e. has a radius of curvature much greater than the initial radius of curvature of the cornea itself) that the first point of contact is at the corneal and lens apex. Occasionally, some light contact at the periphy could occur first or simultaneously, but it is generally of such nature that the cornea under this more peripheral contact region could give way quickly and sufficiently to allow the apical contact to take place and proceed to reshape the central cornea. This is the basis for improving central/foveal focus by correction of the central refractive error.

When this phenomenon is coupled with the requirement of repositioning the peripheral image point, as computed using the methods described above, the amount of asphericity (e.g. shape factor) is usually large. Thus, occasionally to frequently, depending on the amount of correction and peripheral refocusing to be achieved, the first contact between the cornea and lens would be at the junction of the optic zone and alignment curve (the outer curve applied to a lens to ensure correct alignment and centration of the lens to the cornea), and this could occur with such magnitude that the corneal apex does not receive sufficient treatment to correct the central refractive error.

This condition may be readily identified by applying the following test. Using standard sagittal height (or surface altitude, often abbreviated to "sag") formulas familiar to lens designers and optical engineers, the sags of the cornea and the targeted back surface asphericity are calculated for the intended lens zone size. When the cornea has a smaller sag height than the targeted aspheric surface, then the effect described in the previous paragraph exists and must be dealt with.

In the present invention, an additional method for the design of a lens to achieve the dual objective of central correction and peripheral refocusing, is to consider the design in a two-zone approach. The central optical zone would be configured in such as way that this central optical zone will not have the total amount of asphericity (e.g. shape factor) needed to also effect peripheral refocusing. (Indeed, this optic zone may even have no asphericity similar to conventional orthokeratology lenses, or perhaps even be prolate.)

The asphericity of the back surface is then started at the location corresponding to a novel peripheral therapeutic zone. This zone will be configured with the appropriate asphericity to provide the appropriate local radius of the back surface to effect peripheral refocusing.

The junction and transition between the central optic zone and the peripheral therapeutic zone may be blended to improve comfort and remove severe local changes in mechanical pressures on the cornea (i.e. ensure 'smoothness' of the mechanical effect).

Despite the aforegoing considerations of a two-zone approach, it is emphasised that regardless of the number of zones and their sizes (diameters), the features that are key to achieving the objectives of the present invention are the central and local peripheral radii of curvature. The use of aspheric surfaces serves to maintain a continuous surface between these radii to maximise comfort and minimise mechanical pressure abruptness.

The following examples illustrate how the steps described in the above methods for computation of key design parameters and translation of these parameters to the final design may be combined in order to achieve a device of the present invention for specific individual patients.

EXAMPLE 2

A myopic patient is to be treated by applying a device of the current invention. The procedure described in FIG. 1 was followed making use of the more precise computer-assisted ray-tracing method. The patient was measured for central distance refraction (with a result of −4.00 D) using clinical refraction techniques understood by ophthalmic practitioners. Then the patient was measured for corneal shape using a corneal topography system typically available in ophthalmic clinics (e.g. a videokeratograph). In this example, the corneal shape was summarised by the corneal topography output as having a central radius of $R_0$=7.70 mm with a shape factor of p=0.80. Next the peripheral refraction of the patient was measured using standard refraction equipment and techniques but with the additional step of instructing the patient to gaze 'side on' to the refraction instrument. In this example, the peripheral refraction was measured at the field angle of 35° and found to be −3.00 D (i.e. the peripheral refraction is relatively more hyperopic by +1.00 D than the central refraction).

Figure 5:
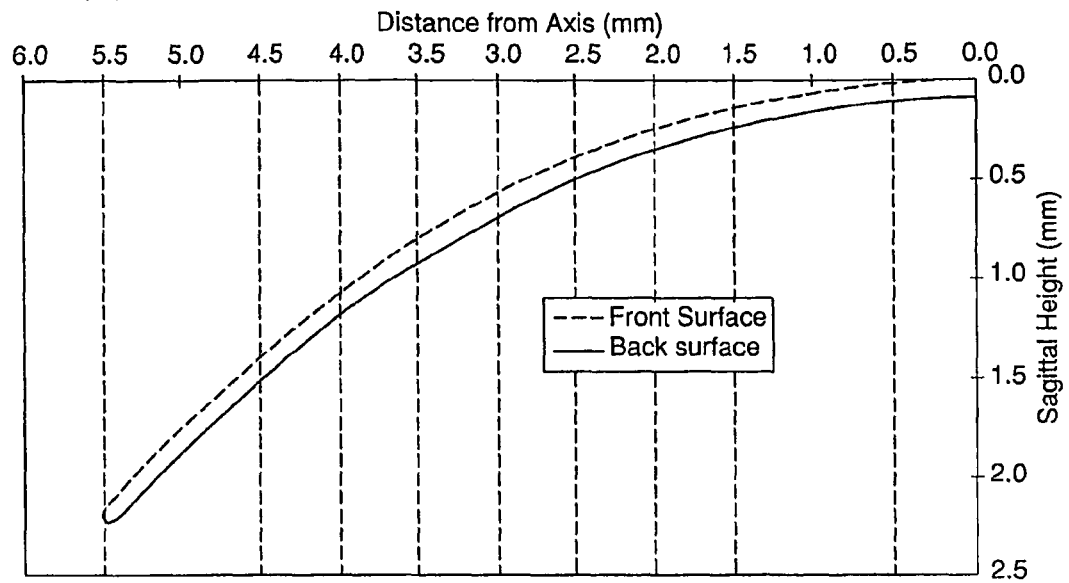
FIGS. 5 to 7 show cross-sectional views of lenses produced in accordance with the methods of the invention.

A computer-assisted ray-tracing model (as described in the previous sections) was set up to incorporate the measured parameters for the patient (i.e. central and peripheral refraction, peripheral field angle, corneal shape parameters). In this example, it was decided to provide the minimum myopic therapy effect. Thus, the device design parameters were calculated for changing the corneal shape to correct both the central and peripheral refractive state without introducing additional peripheral myopic defocus. From the ray-tracing model's standpoint, the merit function was set up to minimise image blur circle size while correcting for −4.00 D along the axis and −3.00 D at 35° field angle. Optimisation of the model according to this merit function returned a design for the back surface (including the central optical correction zone and the peripheral therapeutic zone) with central radius $r_o$ of 8.391 mm and a shape factor of 2.537. The back surface design incorporating these design parameters as well as additional peripheral and edge design parameters to facilitate centration of the device with the eye, apply the appropriate mechanical effect on the cornea in order to reshape the cornea, as well as improving comfort is applied as described under the previous section. The resultant final design for reshaping the cornea of this example is shown in FIG. 5. Table 1 show ones possible contact lens prescription that can achieve the lens required for this example.

TABLE 1

| DOCTOR'S NAME | PATIENT IDENTIFIER | DATE & TIME | File Name NAME | LASER MARK | TARGET POWER +/-XX.XXX | TARGET DIAMETER XX.XX | MATERIAL CODE xxx x x.xx | ZONES |
|---|---|---|---|---|---|---|---|---|
| MC Paragon cm 7.7 p0.8 | 770_.8, 35° R, A-4, B-3/OU | July 29, 2007 3:29 PM | 21265907 | 84 110 +0 | 0.000 | 11.00 | 100 W | 4 |

| ACTUAL POWER +/-X.XXXX | HARMONIC MEAN THICKNESS 0.XXX | Dk/t XX.X | TOTAL SURFACE AREA (mm²) XXX | ACTUAL DIAMETER XX.XX | CENTER THICKNESS 0.XXX | J1 THICKNESS 0.XXX | BASE CURVE MAX SAG X.XXX | EDGE LENGTH X.XX |
|---|---|---|---|---|---|---|---|---|
| −0.001 | 0.102 | 97.4 | 220 | 11.00 | 0.095 | 0.096 | 2.126 | 0.20 |

| | BASE CURVE RADIUS X.XXXX | BASE CURVE WIDTH X.XXX | BASE CURVE SHAPE FACTOR X.XX | FRONT CURVE RADIUS X.XXXX | FRONT CURVE WIDTH XX.XX | FRONT CURVE SHAPE FACTOR X.XX | BASE CURVE SAG X.XXXX | FRONT CURVE SAG X.XXXX | FRONT JUNCTION THICKNESS 0.XXX |
|---|---|---|---|---|---|---|---|---|---|
| 1st | 8.390 | 1.500 | 2.537 | 8.420 | 3.000 | 1.000 | 0.232 | 0.553 | 0.095 |
| 2nd | 8.390 | 1.500 | 2.537 | 7.340 | 1.250 | 0.600 | 0.684 | 1.223 | 0.120 |
| 3rd | 7.470 | 0.600 | 0.600 | 7.570 | 1.000 | 0.600 | 0.966 | 1.942 | 0.110 |
| 4th | 7.470 | 0.000 | 0.600 | 7.570 | 0.000 | 0.600 | 0.966 | 1.942 | 0.110 |
| 5th | 7.470 | 0.000 | 0.600 | 7.570 | 0.000 | 0.600 | 0.966 | 1.942 | 0.110 |
| 6th | 7.470 | 0.000 | 0.600 | 7.570 | 0.000 | 0.600 | 0.966 | 1.942 | 0.110 |
| 7th | 7.470 | 0.000 | 0.600 | 7.570 | 0.000 | 0.600 | 0.966 | 1.942 | 0.110 |
| 8th | 7.470 | 0.000 | 0.600 | 7.570 | 0.000 | 0.600 | 0.966 | 1.942 | 0.110 |
| 9th | 7.470 | 0.000 | 0.600 | 7.570 | 0.000 | 0.600 | 0.966 | 1.942 | 0.110 |
| 10th | 7.470 | 1.710 | 0.600 | 7.570 | 0.060 | 0.600 | 2.123 | 1.992 | 0.100 |

When this device is applied to the patient's eye in an orthokeratology procedure, the device will provide correct distance vision as well as eliminate the peripheral stimulus for myopia progression.

Depending on the patient's individual response, it may be necessary to adjust or fine-tune the parameters of the device. Hence, the patient's progress with the device of the above design parameters will be monitored including periodic measurements of central and peripheral refractive states as described in the flowchart depicted in FIG. 1.

EXAMPLE 3

A patient was found to have −8.00 D of myopia (i.e. central refractive state). It was decided to treat her progression of myopia by orthokeratology using the device of this invention. In this example, the ophthalmic practitioner did not have access to a corneal topography system (e.g. videokeratograph) and peripheral refractive state measurement was not available for the particular patient. As a starting point for estimating the corneal shape, with the unavailability of a corneal topography, a keratometer was used to measure the central radius of curvature of the cornea. (A keratometer is a commonly available ophthalmic clinical instrument for measuring central corneal curvature. While in actuality, the keratometer measures an average radius around the central corneal region, this value is close enough to the central radius $R_o$ of a cornea for the current purpose of arriving at an approximate shape for the cornea as a starting point.) The keratometer found a radius of 7.80 mm. The population average (based on many published scientific literature values) shape factor of p=0.75 was assumed for this patient. In the absence of direct peripheral refraction measurements, the peripheral refractive state of this patient was assumed to be the typical published value for a −8.00 D myope. Thus a value of −7.00 D was assumed for the peripheral refractive state (i.e. +1.00 D more hyperopic relative to central refraction). In this example, it was decided to enhance the myopia therapy effect by introducing an additional amount of myopic peripheral defocus of +1.00 D.

The practitioner of this example did not have access to computer programs for ray-tracing an eye model. Hence, the approximate formula for calculating the starting design parameters was used. Thus from the above parameter values, we have for the equations from the previous section:

$A$=central refraction=−8.00 $D$ $B$=peripheral refraction=−7.00 $D$ $D$=myopic peripheral defocus=+1.00 $D$ θ=field angle of peripheral refraction=35°

$R_o$=7.80 mm p=0.75

Putting these values into the above equation returns a target central radius for the back surface of $R_o$=9.357 mm and shape factor p=4.157.

While these design parameter values are not as precise as those calculable using a ray-tracing model, they are sufficiently close as to provide good starting design parameter values for a device for initiating myopia therapy for this patient.

Figure 6:
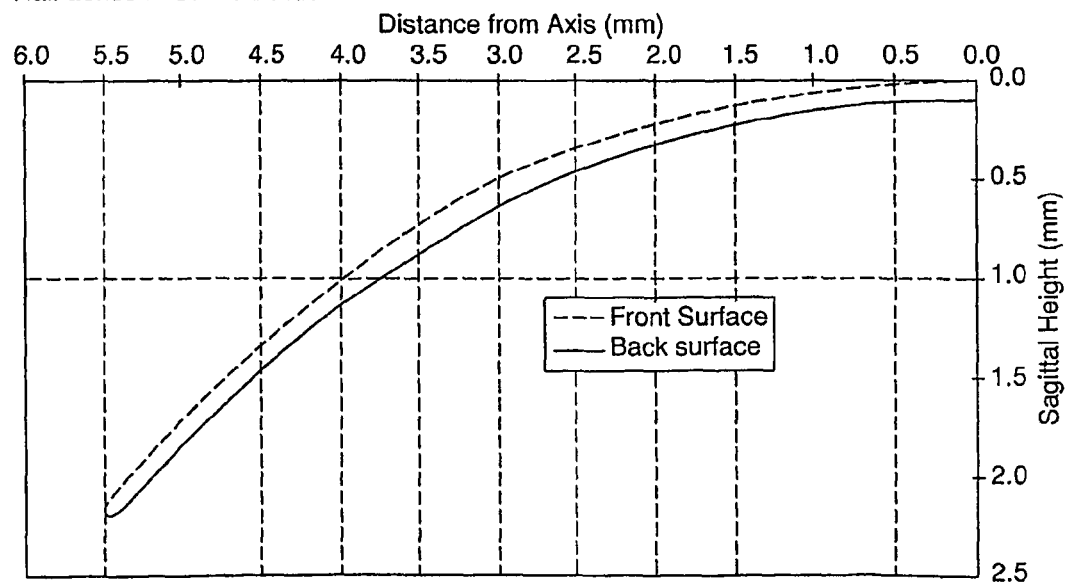

As for Example 2, the back surface design incorporating these design parameters, as well as additional peripheral and edge design parameters to facilitate centration of the device with the eye, apply the appropriate mechanical effect on the cornea in order to reshape the cornea, as well as improving comfort is calculated according to the steps described above. The resultant final lens design is given in FIG. 6 and an example of a prescription table in Table 2.

TABLE 2

| DOCTOR'S NAME | PATIENT IDENTIFIER | DATE & TIME | File Name NAME | LASER MARK | TARGET POWER +/-XX.XXX | TARGET DIAMETER XX.XX | MATERIAL CODE xxx x x.xx | ZONES |
|---|---|---|---|---|---|---|---|---|
| MC Paragon cm 7.8 p0.75 | 780_.75, 35° E, A-8, B-6/OU | July 29, 2007 4:02 PM | 20903452 | 94 110 +0 | 0.000 | 11.00 | 100 W | 4 |

| ACTUAL POWER +/-X.XXXX | HARMONIC MEAN THICKNESS 0.XXX | Dk/t XX.X | TOTAL SURFACE AREA (mm²) XXX | ACTUAL DIAMETER XX.XX | CENTER THICKNESS 0.XXX | J1 THICKNESS 0.XXX | BASE CURVE MAX SAG X.XXX | EDGE LENGTH X.XX |
|---|---|---|---|---|---|---|---|---|
| 0.000 | 0.106 | 94.1 | 220 | 11.01 | 0.095 | 0.097 | 2.090 | 0.20 |

| | BASE CURVE RADIUS X.XXXX | BASE CURVE WIDTH X.XXX | BASE CURVE SHAPE FACTOR X.XX | FRONT CURVE RADIUS X.XXXX | FRONT CURVE WIDTH XX.XX | FRONT CURVE SHAPE FACTOR X.XX | BASE CURVE SAG X.XXXX | FRONT CURVE SAG X.XXXX | FRONT JUNCTION THICKNESS 0.XXX |
|---|---|---|---|---|---|---|---|---|---|
| 1st | 9.357 | 1.500 | 4.157 | 9.387 | 3.000 | 1.000 | 0.219 | 0.492 | 0.096 |
| 2nd | 9.357 | 1.500 | 4.157 | 7.120 | 1.250 | 0.600 | 0.643 | 1.187 | 0.136 |
| 3rd | 7.320 | 0.600 | 0.500 | 7.420 | 1.000 | 0.500 | 0.928 | 1.906 | 0.120 |
| 4th | 7.320 | 0.000 | 0.500 | 7.420 | 0.000 | 0.500 | 0.928 | 1.906 | 0.120 |
| 5th | 7.320 | 0.000 | 0.500 | 7.420 | 0.000 | 0.500 | 0.928 | 1.906 | 0.120 |
| 6th | 7.320 | 0.000 | 0.500 | 7.420 | 0.000 | 0.500 | 0.928 | 1.906 | 0.120 |
| 7th | 7.320 | 0.000 | 0.500 | 7.420 | 0.000 | 0.500 | 0.928 | 1.906 | 0.120 |
| 8th | 7.320 | 0.000 | 0.500 | 7.420 | 0.000 | 0.500 | 0.928 | 1.906 | 0.120 |
| 9th | 7.320 | 0.000 | 0.500 | 7.420 | 0.000 | 0.500 | 0.928 | 1.906 | 0.120 |
| 10th | 7.320 | 1.710 | 0.500 | 7.420 | 0.060 | 0.500 | 2.087 | 1.956 | 0.100 |

When this device is applied to the patient's eye in a corneal reshaping procedure, the device will provide correct distance vision as well as reduce or eliminate the peripheral stimulus for myopia progression.

Also as in Example 2, and perhaps more importantly since only an approximate starting design was used, it may be necessary to adjust or fine-tune the design parameters of the device following some initiate wearing/treatment period by the patient. Hence, the patient's progress with the device of the above design parameters will be monitored including periodic measurements of central and peripheral refractive states as described in the flowchart shown in FIG. 1.

EXAMPLE 4

A patient was found to have −6.00 D of myopia. As in the previous example, the practitioner did not have access to a corneal topography system and peripheral refractive state measurement was not available for the particular patient. Thus, a keratometer was used to measure the central radius of curvature of the cornea. The keratometer found a radius of 7.80 mm. From published population average, a shape factor of p=0.75 was assumed for this patient. The peripheral refractive state of this patient was assumed to be the typical published value for a −6.00 D myope. Thus a value of −5.00 D was assumed for the peripheral refractive state. In this example, it was decided to enhance the myopia therapy effect by introducing an additional amount of myopic peripheral defocus of +0.50 D. In this case, a peripheral field angle of 25° was planned as the starting field angle of therapy.

Again, as in the previous example, ray-tracing software for computing an eye model was not available. Hence, the approximate formula for calculating the starting design parameters was used:

$A$=central refraction=−6.00 $D$ $B$=peripheral refraction=−5.00 $D$ $D$=myopic peripheral defocus=+0.50 $D$ $\theta$=field angle of peripheral refraction=25°

$R_o$=7.80 mm p=0.75

Putting these values into the system of equations from the previous section returns a target central radius for the back surface of $R_o$=8.912 mm and shape factor p=5.268.

These key parameters were translated into the final lens design according to the steps described in a previous section. As discussed under the section "Definition of Zones", it was found in this example that, due to the large amount of asphericity required of this back surface, a two-zone approach would eliminate the problem associated with peripheral zone contact with the peripheral cornea (which reduces the treatment effect over the central cornea required for correcting central refractive error).

Figure 7:
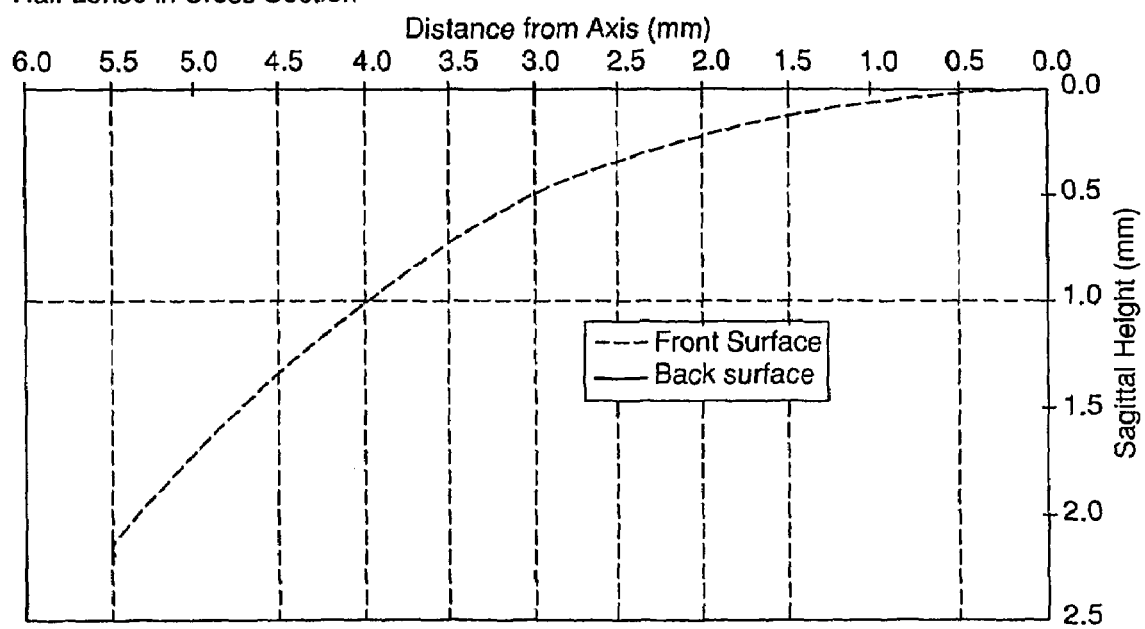

Hence, a two-zone design approach, as described above was adopted. The resultant final lens design consisting of a central optical zone and a peripheral therapeutic zone, is given in FIG. 7. An example lens prescription table for this final lens design is given in Table 3. In Table 3, it can be seen that the central optic zone (row labelled as "1$^{st}$") has a shape factor of p=0 indicating it is a conventional spherical surface optical zone. However, the next zone, being the peripheral therapeutic zone, has the shape factor calculated according to the above (i.e. 5.268).

TABLE 3

| DOCTOR'S NAME | PATIENT IDENTIFIER | DATE & TIME | File Name NAME | LASER MARK | TARGET POWER +/−XX.XXX | TARGET DIAMETER XX.XX | MATERIAL CODE xxx x x.xx | ZONES |
|---|---|---|---|---|---|---|---|---|
| MC Paragon cm 7.8 p0.75 | 780_.75, 25° E, A-6, B-45/OU | July 29, 2007 5:00 PM | 20544719 | 89 110 +0 | 0.000 | 11.00 | 100 W | 4 |

| ACTUAL POWER +/−X.XXXX | HARMONIC MEAN THICKNESS 0.XXX | Dk/t XX.X | TOTAL SURFACE AREA (mm$^2$) XXX | ACTUAL DIAMETER XX.XX | CENTER THICKNESS 0.XXX | J1 THICKNESS 0.XXX | BASE CURVE MAX SAG X.XXX | EDGE LENGTH X.XX |
|---|---|---|---|---|---|---|---|---|
| 0.000 | 0.103 | 96.5 | 217 | 10.99 | 0.095 | 0.092 | 2.054 | 0.20 |

| | BASE CURVE RADIUS X.XXXX | BASE CURVE WIDTH X.XXX | BASE CURVE SHAPE FACTOR X.XX | FRONT CURVE RADIUS X.XXXX | FRONT CURVE WIDTH XX.XX | FRONT CURVE SHAPE FACTOR X.XX | BASE CURVE SAG X.XXXX | FRONT CURVE SAG X.XXXX | FRONT JUNCTION THICKNESS 0.XXX |
|---|---|---|---|---|---|---|---|---|---|
| 1st | 8.912 | 2.500 | 1.000 | 8.942 | 3.000 | 1.000 | 0.453 | 0.518 | 0.092 |
| 2nd | 8.912 | 0.500 | 5.268 | 7.200 | 1.250 | 0.600 | 0.672 | 1.204 | 0.140 |
| 3rd | 7.300 | 0.600 | 0.300 | 7.400 | 1.000 | 0.300 | 0.953 | 1.890 | 0.123 |
| 4th | 7.300 | 0.000 | 0.300 | 7.400 | 0.000 | 0.300 | 0.953 | 1.890 | 0.123 |
| 5th | 7.300 | 0.000 | 0.300 | 7.400 | 0.000 | 0.300 | 0.953 | 1.890 | 0.123 |
| 6th | 7.300 | 0.000 | 0.300 | 7.400 | 0.000 | 0.300 | 0.953 | 1.890 | 0.123 |
| 7th | 7.300 | 0.000 | 0.300 | 7.400 | 0.000 | 0.300 | 0.953 | 1.890 | 0.123 |
| 8th | 7.300 | 0.000 | 0.300 | 7.400 | 0.000 | 0.300 | 0.953 | 1.890 | 0.123 |
| 9th | 7.300 | 0.000 | 0.300 | 7.400 | 0.000 | 0.300 | 0.953 | 1.890 | 0.123 |
| 10th | 7.300 | 1.700 | 0.300 | 7.400 | 0.050 | 0.300 | 2.055 | 1.929 | 0.099 |

It is important to emphasise that the important variable is not the asphericity of the eye that is corrected by the method of the invention. The lens of the invention is changing the focus of the peripheral rays coming into the eye from a selected field angle which is typically above about 20°. The important design variable is, accordingly, the local radii of curvature of the reshaped cornea (and hence, the lens back surface) at the position that corresponds to light rays from the peripheral field angle. Hence, by understanding the optimal shape of the cornea post treatment, particularly the shape of the cornea in the peripheral region of the eye the back surface of the treatment lens can be accurately modelled and shaped.

In essence the method steps calculate the existing focal length (or refractive power) of the natural cornea by calculating the local radius at the centre and at the periphery. This is done implicitly in the case of ray-tracing (method 1) and explicitly by the equation method (method 2). From this and the known (either by measurement or estimate) central and peripheral refractive states of the natural eye, it can be calculated how much power needs to be added or subtracted at centre and periphery. From these calculated shape variations the new/required power at the centre and the periphery can be calculated. From these target powers, the respective target centre radius ($R'_0$) and target peripheral radii ($R'_s$ and $R'_t$) can be calculated.

It is important to note that there are two radii for the periphery. This is due to the known optical aberration called "oblique astigmatism" or "radial astigmatism" whereby there isn't a single sharp focal point for a peripheral image, but in effect, two different (line shaped rather than point shaped) foci (at right angles to each other). These foci are the sagittal and tangential foci of astigmatism. For each of these sagittal and tangential focus, there is a sagittal and tangential refractive power and a respective sagittal and tangential radius of curvature. The average of the two astigmatic powers is the mean power. This mean power is the 'average peripheral power' ($F_p$ and $F'_p$ in the above equation) which is the nearest average focus for the eye at that peripheral field angle.

In practice, when the cornea is reshaped, typically the design for the cornea (and associated orthokeratology lens designs) only defines the tangential radius of curvature. This is because the sagittal radius is governed more or less by the rotational symmetry of the lens being made on a lathe. Thus, a local radius at a given point on a lens's surface is calculated, it is the cross-sectional radius, which is the tangential radius that is calculated. In the equation method (method 2), it is the mean power needed that is calculated. The tangential and sagittal power are then estimated from a "rule-of-thumb" calculation which has been verified by research on the "zonal compensation factor" that works best. From this, the asphericity is calculated. In the ray-tracing method (method 1), the initial assumption is that the surface is one form (of any of a number of) type of aspheric surface (such as a conics section, polynomial, etc). Once the appropriate assumptions and approximations have been made the software and processor are used to find the best fit asphericity that will give the appropriate mean power.

Figure 8:
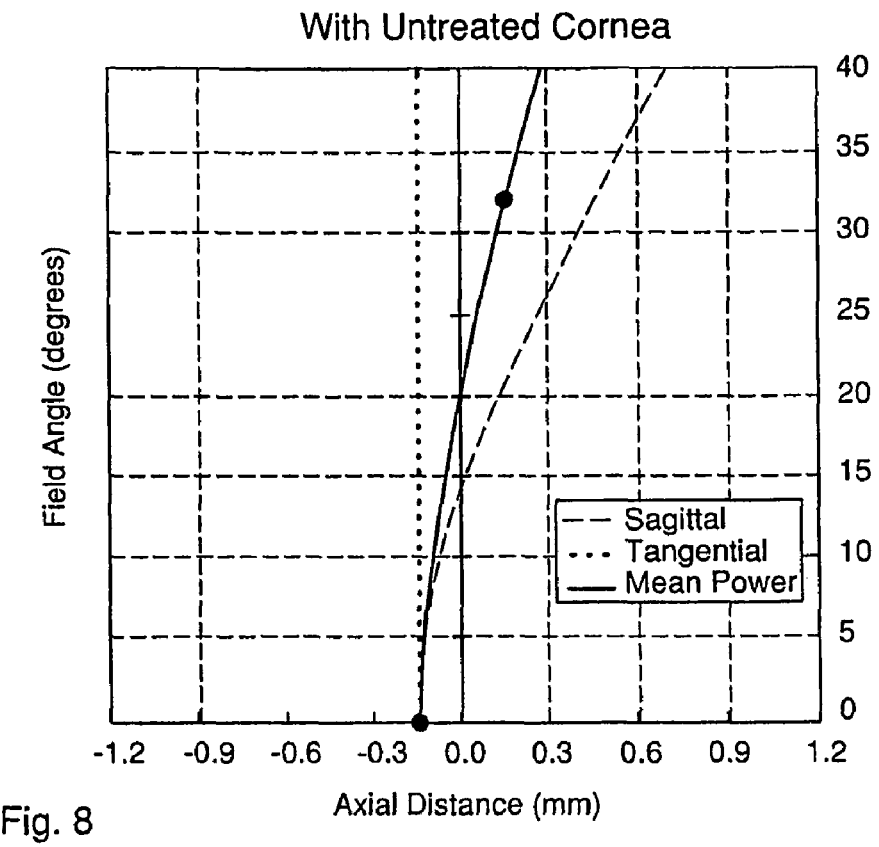
FIGS. 8 and 9 show diagrammatic depictions of the focus of an eye before and after treatment according to the invention.

FIG. 8 is a relative curvature of field plot illustrating the image surface of a myope with relatively hyperopic defocus in the periphery. The vertical axis at Axial Distance=0 mm represents the retina. Curvature of field is seen as a change in the image surface position relative to the retina as field angle increase. For example, when this patient is measured for central refraction (lower black diamond) the image point is in front of (negative axial distance) the retina and approximately −0.50 D of myopia would be measured. However, when refraction is carried out at a field angle of e.g. 32° (upper black diamond), the focal position here is behind the retina and hyperopia of around +0.50 D would be measured. According to the teachings of Smith, it is this hyperopic defocus in the periphery that stimulus eye ball growth leading to myopia progression.

Figure 9:
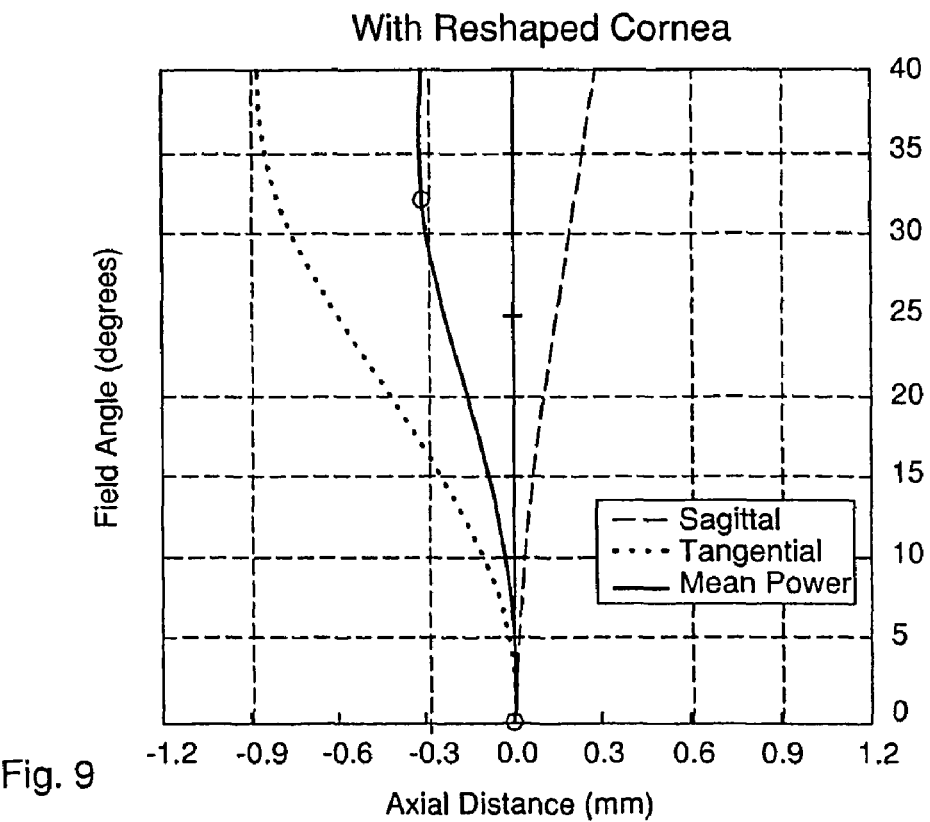

FIG. 9 shows a relative curvature of field plot similar to FIG. 8. Here, the eye of FIG. 8 has been treated by reshaping of the anterior corneal surface employing the method and lens design of the present invention. It can be seen that the central image point represented by lower black diamond now lies on the retina indicating central refractive error has been effective corrected. Further, due to the manipulation of the peripheral corneal shape of the present invention, the more peripheral image points (e.g. upper black diamond at 32° field, angle) now lies in front of the retina. (For example, a refraction carried out at this peripheral field angle would return approximately +1.00 D.) By placing the peripheral image point on or in front of the retina, the stimulus for eye growth has been reduced or eliminated, thereby retarding myopia progression.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

The invention claimed is:

1. A corneal contact lens including a lens body having anterior and posterior surfaces, and wherein the posterior surface is configured to be placed in contact with a cornea of a wearer's eye and, in use, to alter the shape of the cornea of the wearer's eye, the posterior surface comprising:
   central treatment zone having a concave shape adapted to shape the central region of the cornea to a configuration which will result in axial light entering the eye being focused on the retina of the wearer;
   an annular peripheral treatment zone adjacent and contiguous with the central treatment zone and adapted to shape the cornea in the peripheral region of the cornea to a configuration which will result in peripheral light entering the eye being focused at a position anterior of the retina; and
   an annular centration zone surrounding the peripheral treatment zone and adapted to mechanically locate the lens with respect to the eye.

2. A lens according to claim 1, wherein the posterior surface of the lens is configured alter the shape of the cornea of the wearer to both therapeutically regress the progression of myopia, and simultaneously correct for myopic refractive error.

3. A lens according to claim 1, wherein the central treatment zone is optically active.

4. A lens according to claim 1, wherein the annular peripheral treatment zone is optically active.

5. A lens according to claim 1, wherein the annular centration zone is optically inactive.

6. A lens according to claim 1, wherein the central treatment zone is adapted to overlie a central optical region of the eye, the central treatment zone having a radius of curvature which is greater than a radius of curvature of the central optical region of the eye.

7. A lens according to claim 1, wherein the annular peripheral treatment zone is adapted to overlie a peripheral optical region of the eye, the peripheral treatment zone having a radius of curvature which is less than a radius of curvature of the central treatment zone.

8. A lens according to claim 1, wherein the annular centration zone has a shape which approximates the configuration of the eye in the region of the eye radially outwards of a peripheral optical region of the eye.

9. A lens according to claim 1, wherein the configurations of the central treatment zone and the annular peripheral treatment zones are selected such that in use the epithelial volume of the eye will be retained during treatment.

10. A lens according to claim 1, wherein the anterior surface of the lens provides the lens with a non-zero power.

11. A lens according to claim 10, wherein the non-zero power provides overshoot for the correction of myopia.

12. A mould for altering the shape of a patient's cornea comprising a central optic zone, a peripheral optic zone, and a peripheral mechanical zone wherein said central optic zone is generally circular, and comprises a generally concave back surface, said concave back surface of said central optic zone is selected according to the patient's corneal topography and central refractive state to induce a specific desired alteration in the patient's central corneal topography to produce a correction of the patient's central refractive state and wherein said peripheral optic zone is generally annular and surrounds the central optic zone, and comprises a generally concave back surface; the curvature of said concave back surface of said peripheral optic zone is selected according to the patient's corneal topography to induce a specific desired alteration in the patient's peripheral corneal topography to produce a resultant peripheral refractive state; said resultant peripheral refractive state being relatively more myopic than said central refractive state and wherein said peripheral mechanical zone is generally annular and surrounds the peripheral optic zone, the curvature of the back surface of said peripheral mechanical zone is selected to facilitate alignment and centration of the mould with the patient's cornea.

13. The mould according to claim 12, having a cross-sectional diameter from periphery to periphery of between about 8.0 and 13.0 mm.

14. The mould according to claim 12, wherein the diameter of the central optic zone is between about 3 mm and 6 mm.

* * * * *